United States Patent
Qu et al.

(10) Patent No.: US 12,404,526 B2
(45) Date of Patent: Sep. 2, 2025

(54) ENHANCING AGENTS FOR IMPROVED CELL TRANSFECTION AND/OR rAAV VECTOR PRODUCTION

(71) Applicant: Spark Therapeutics, Inc., Philadelphia, PA (US)

(72) Inventors: Guang Qu, Sicklerville, NJ (US); Lin Lu, Wayne, PA (US); Jesusa Josue-Almqvist, Havertown, PA (US); John Fraser Wright, Princeton, NJ (US)

(73) Assignee: SPARK THERAPEUTICS, INC., Philadelphia, PA (US)

( * ) Notice: Subject to any disclaimer, the term of this patent is extended or adjusted under 35 U.S.C. 154(b) by 0 days.

(21) Appl. No.: 16/619,898

(22) PCT Filed: Jun. 6, 2018

(86) PCT No.: PCT/US2018/036344
§ 371 (c)(1),
(2) Date: Dec. 5, 2019

(87) PCT Pub. No.: WO2018/226887
PCT Pub. Date: Dec. 13, 2018

(65) Prior Publication Data
US 2020/0165632 A1    May 28, 2020

Related U.S. Application Data

(60) Provisional application No. 62/531,626, filed on Jul. 12, 2017, provisional application No. 62/516,432, filed on Jun. 7, 2017.

(51) Int. Cl.
C12N 15/87 (2006.01)
C12N 5/073 (2010.01)

(52) U.S. Cl.
CPC .......... *C12N 15/87* (2013.01); *C12N 5/0603* (2013.01); *C12N 2750/14143* (2013.01); *C12N 2750/14151* (2013.01)

(58) Field of Classification Search
CPC .................. C12N 15/87; C12N 5/0603; C12N 2750/14143; C12N 2750/14151; C12N 15/86; C12N 15/63; C12N 15/09
See application file for complete search history.

(56) References Cited

U.S. PATENT DOCUMENTS

| 2011/0020927 A1 | 1/2011 | Yamaguchi et al. |
| 2011/0212526 A1 | 9/2011 | Hu et al. |
| 2013/0316400 A1 | 11/2013 | Vasu et al. |

FOREIGN PATENT DOCUMENTS

| CN | 104936986 A | 9/2015 |
| JP | 2011-512851 T | 4/2011 |
| JP | 2017-512058 T | 5/2017 |
| RU | 2588667 C2 | 6/2011 |
| WO | 2009/112245 | 9/2009 |
| WO | 2013/079973 A1 | 6/2013 |
| WO | 2014/127185 A1 | 8/2014 |
| WO | 2014/152508 A1 | 9/2014 |
| WO | 2015/031686 A1 | 3/2015 |
| WO | 2015/031686 A9 | 3/2015 |
| WO | 2015/127391 A1 | 8/2015 |
| WO | 2016/075278 A1 | 5/2016 |
| WO | 2017/011598 A1 | 1/2017 |
| WO | 2017/191274 A2 | 11/2017 |

OTHER PUBLICATIONS

Fan et al. "Valproic acid enhances gene expression from viral gene transfer vectors." Journal of virological methods 125.1 (2005): 23-33 (Year: 2005).*

Liu et al. "Sustained FVIII expression and phenotypic correction of hemophilia A in neonatal mice using an endothelial-targeted sleeping beauty transposon." Molecular Therapy 13.5 (2006): 1006-1015 (Year: 2006).*

Chahal, P.S., et al., Production of adeno-associated virus (AAV) serotypes by transient transfection of HEK293 cell suspension cultures for gene delivery, J. Virol. Methods., Nov. 13, 2013, pp. 163-173, vol. 196.

Dai, Z., et al., Elucidating the interplay between DNA-condensing and free polycations in gene transfection through mechanistic study of linear and branched PEI, Biomaterials, Jul. 15, 2011, pp. 8626-8634, vol. 32, No. 33, Elsevier, Amsterdam, NL.

(Continued)

*Primary Examiner* — Fereydoun G Sajjadi
*Assistant Examiner* — Alexander W Nicol
(74) *Attorney, Agent, or Firm* — Baker Botts LLP

(57) ABSTRACT

Provided are compositions and methods of transducing/transfecting cells with a molecule, such as a nucleic acid (e.g., plasmid), at high efficiency. High efficiency transduced/transfected cells can, when transduced with a nucleic acid that encodes a protein or comprises a sequence that is transcribed into a transcript of interest, produce high amounts of protein and/or transcript. High efficiency transduced/transfected cells can, when transduced with plasmids comprising (i) nucleic acids encoding AAV packaging proteins and/or nucleic acids encoding helper proteins; and (ii) a transgene that encodes a protein or is transcribed into a transcript of interest; produce high amounts of recombinant rAAV vector.

37 Claims, 10 Drawing Sheets
Specification includes a Sequence Listing.

(56) References Cited

OTHER PUBLICATIONS

Gray, SJ et al., Production of Recombinant Adeno-Associated Viral Vectors and Use in In Vitro and In Vivo Administration. Current Protocols in Neuroscience. Oct. 2011; Chapter 4, Unit 4.17; pp. 1-36; p. 2, paragraph 2; p. 6, step 12-p. 7, step 27.

Sinhadri, BCS, Effect of Valproic Acid on Transient Protein Expression in HEK 293E Suspension Adapted Cells [online]. Uppsala Universitat. 2009; downloaded from the internet <https://www.ibg.uu.se/digitalAssets/169/c_169881-1_3-k_sindhari-balaji-report.pdf>; pp. 1-26; p. 9, paragraphs 1-p. 10, paragraph 1; p. 15, paragraph 1.

Cai, J., et al., Quantitative Study of Effects of Free Cationic Polyethylenimine Chains on Intracellular Trafficking of DNA/Polymer Polyplexes, Cytotherapy, 2014, vol. 16, Supplement, pp. S32-S33.

Wulhfard, S.L., et al., Valproic acid enhances recombinant mRNA and protein levels in transiently transfected Chinese hamster ovary cells, Journal of Biotechnology, May 14, 2010, 148:128-132.

Yue, Y., et al., Revisit complexation between DNA and polyethylenimine—Effect of length of free polycationic chains o gene transfection, 1Journal of Controlled Release, Mar. 7, 2011, 152:143-151.

Samulski, R.J., et al., AAV-Mediated Gene Therapy for Research and Therapeutic Purposes, Annu. Rev. Virol., 2014, 1:427-51, downloaded from www.annualreviews.org access provided by 204.227.255.5 on Aug. 8, 2022.

Cervera et al., "Selection and optimization of transfection enhancer additives for increased virus-like particle production in HEK293 suspension cell cultures," Appl Microbiol Biotechnol 99:9935-9949 (2015).

Backliwal, G., et al., Valproic Acid: A Viable Alternative to Sodium Butyrate for Enhancing Protein Expression in Mammalian Cell Cultures, Biotechnology and Bioengineering, Mar. 7, 2008, vol. 101, No. 1, pp. 182-189.

"ExpiFectamine™ 293 Transfection Kits," Gibco Product Information Sheet, Oct. 30, 2015, 4 pgs.

Grieger et al., "Production of Recombinant Adeno-associated Virus Vectors Using Suspension HEK293 Cells and Continuous Harvest of Vector From the Culture Media for GMP FIX and FLT1 Clinical Vector," 24(2):287-297 (2016).

* cited by examiner

ENHANCING AGENTS FOR IMPROVED CELL TRANSFECTION AND/OR rAAV VECTOR PRODUCTION

RELATED APPLICATION INFORMATION

This patent application is the National Phase of International Application No. PCT/US2018/036344, filed Jun. 6, 2018, which designated the U.S. and that International Application was published under PCT Article 21 (2) in English, which claims the benefit of priority to U.S. Provisional Patent Application No. 62/516,432, filed Jun. 7, 2017, and U.S. Provisional Patent Application No. 62/531,626, filed Jul. 12, 2017. The entire contents of the foregoing applications are incorporated herein by reference, including all text, tables, sequence listing and drawings.

SEQUENCE LISTING

The instant application contains a Sequence Listing which has been submitted electronically in ASCII format and is hereby incorporated by reference in its entirety. Said ASCII copy, created on Dec. 4, 2019, is named "023637-0508883_ST25.txt" and is 13.4 KB in size.

FIELD OF INVENTION

This invention relates to the fields of cell transduction (transfection) with nucleic acid, e.g., plasmids. More particularly, the invention provides compositions and methods for producing transduced (transfected) cells, said cells optionally producing Adeno-Associated Viral (rAAV) Vector.

INTRODUCTION

Several publications and patent documents are cited throughout the specification in order to describe the state of the art to which this invention pertains. Each of these citations is incorporated herein by reference as though set forth in full.

SUMMARY

The invention provides compositions of and methods for transfecting cells with at least one nucleic acid sequence. In one embodiment, a transfection composition or method includes: (a) contacting cells with at least one nucleic acid formulated with a solution comprising polyethylenimine (PEI); (b) incubating or culturing the cells with the nucleic acid and polyethylenimine (PEI) solution; (c) adding an enhancing agent at the time of or immediately after step (a) or up to but less than 3 hours after step (a) to produce a mixture; and (d) incubating said mixture of step (c) thereby transfecting the cells with the nucleic acid sequence.

The invention also provides compositions of and methods for making cells that produce recombinant viral vectors, such as rAAV vector. In one embodiment, a composition or method includes: (a) providing a PEI/plasmid mixture of components (i), (ii) and (iii), in which (i) is one or more plasmids comprising nucleic acids encoding AAV packaging proteins and/or nucleic acids encoding helper proteins; (ii) is a plasmid comprising a transgene that encodes a protein or is transcribed into a transcript of interest; and (iii) is a polyethylenimine (PEI) solution, (b) contacting cells with the plasmid/PEI mixture of step (a) to produce a plasmid/PEI cell culture; (c) adding an enhancing agent to the plasmid/PEI cell culture to produce a second mixture; and (d) incubating said second mixture of step (c) thereby making transfected cells that produce recombinant rAAV vector.

In various further embodiments of the invention compositions and methods, included are one or more additional optional steps.

In a particular aspect, a further step comprises (c) harvesting said transfected cells produced in step (d) and/or culture medium from the transfected cells produced in step (d) to produce a cell and/or culture medium harvest.

In a particular aspect, a further optional step comprises (e) culturing, expanding, isolating or selecting for cells that have been transfected with the nucleic acid or plasmids.

In a particular aspect, a further optional step comprises (e) isolating and/or purifying recombinant AAV vector from the transfected cells produced in step (d) and/or culture medium and/or from the transfected cells produced in step (d).

In a particular aspect, a further optional step comprises (f) isolating and/or purifying recombinant AAV vector from the transfected cells and/or culture medium harvest produced in step (e).

In a further embodiment, the nucleic acid sequence(s) comprises a vector and/or a plasmid.

In a further embodiment, the nucleic acid sequence(s) comprises a viral vector and/or viral plasmid. In a particular aspect, the viral vector or viral plasmid comprises a lentiviral vector or plasmid, or an adeno-associated viral (AAV) vector or plasmid.

In a further embodiment, the vector comprises a transgene that encodes a protein or is transcribed into a transcript of interest. In a particular aspect, the transgene encodes a wild-type, or functional variant blood clotting factor, apoE2, TPP1, argininosuccinate synthase, copper transporting ATPase 2, acid alpha-glucosidase, β-Glucocerebrosidase, α-galactosidase or C1 inhibitor serine protease inhibitor. In a particular aspect, the wild-type, or functional variant blood clotting factor is Factor VII, Factor VIII, or Factor IX.

In a further embodiment, the enhancing agent is added prior to step (a), at the time of step (a) or immediately after step (a).

In a further embodiment, the enhancing agent is added prior to step (a), at the time of step (a) or up to 16 hours after step (a).

In a further embodiment, the enhancing agent is added prior to step (a), at the time of step (a) or up to but less than 3 hours after step (a).

In a further embodiment, the enhancing agent is added prior to step (a), at the time of step (a) the enhancing agent is added two or more times before or after steps (a) or (b).

In a further embodiment, the enhancing agent is first added at the time of or immediately after step (a) or up to 16 hours after step (a) and added again 16-72 hours after steps (a) or (b), or added again 16-48 hours after steps (a) or (b), or added again 16-24 hours after steps (a) or (b).

In a further embodiment, the enhancing agent is first added at the time of or immediately after step (a) or up to but less than 3 hours after step (a) and added again 12-72 hours after steps (a) or (b), or added again 12-48 hours after steps (a) or (b), or added again 12-24 hours after steps (a) or (b).

In a further embodiment, the enhancing agent is first added 12 to 72 hours before step (a) and added again at the time of or immediately after step (a) or up to 16 hours after step (a).

In a further embodiment, the enhancing agent is first added 12 to 72 hours before step (a) and added again at the time of or immediately after step (a) or up to but less than 3 hours after step (a).

In a further embodiment, plasmids (i) and (ii) are in a molar ratio range of about 1:0.01 to about 1:100, or are in a molar ratio range of about 100:1 to about 1:0.01, and wherein the mixture of components (i), (ii) and (iii) has optionally been incubated for a period of time from about 10 seconds to about 4 hours prior to step (b).

In a further embodiment, the nucleic acid or plasmids are in PEI: nucleic acid or PEI: plasmid weight ratio in the range of about 0.1:1 to about 5:1, or in a PEI: nucleic acid or PEI: plasmid weight ratio in the range of about 5:1 to about 0.1:1.

In a further embodiment, the nucleic acid or plasmids are in PEI: nucleic acid or PEI: plasmid weight ratio in the range of about 1:1 to about 5:1, or in a PEI: nucleic acid or PEI: plasmid weight ratio in the range of about 5:1 to about 1:1.

In a further embodiment, the nucleic acid or plasmids are in PEI: nucleic acid or PEI: plasmid weight ratio in the range of about 1:1 to about 3:1.

In a further embodiment, the nucleic acid or plasmids are in PEI: nucleic acid or PEI: plasmid weight ratio in the range of about 1:1, about 1.5:1, about 2:1, about 2.5:1 or about 3:1.

In a further embodiment, the compositions or methods further include adding Free PEI to the cells.

In a further embodiment, Free PEI is added to the cells prior to, at the time of or after steps (a) or (b), or prior to or at the time of or after step (c).

In a further embodiment, Free PEI is added to the cells at the time of or after steps (a) or (b), or at the time of or after step (c).

In a further embodiment, Free PEI is added so that the PEI: nucleic acid or PEI: plasmid weight ratio is in the range of about 0.1:1 to about 5:1, or is in the range of about 5:1 to about 0.1:1.

In a further embodiment, Free PEI is added so that the PEI: nucleic acid or PEI: plasmid weight ratio is in the range of about 1:1 to about 5:1, or in the range of about 5:1 to about 1:1.

In a further embodiment, the PEI in the PEI: nucleic acid and/or PEI: plasmid and/or Free PEI comprises linear polyethylenimine.

In a further embodiment, the PEI in the PEI: nucleic acid and/or PEI: plasmid and/or Free PEI comprises a hydrolyzed linear polyethylenimine.

In a further embodiment, the PEI in the PEI: nucleic acid and/or PEI: plasmid and/or Free PEI comprises a hydrolyzed linear polyethylenimine with a molecular weight in the range of about 4,000 to about 160,000 and/or in the range of about 2,500 to about 250,000 molecular weight in free base form.

In a further embodiment, the PEI in the PEI: nucleic acid and/or PEI: plasmid and/or Free PEI comprises a hydrolyzed linear polyethylenimine with a molecular weight of about 40,000 and/or about 25,000 molecular weight in free base form.

In a further embodiment, the molar ratio of nitrogen (N) in the Total PEI to phosphate (P) in nucleic acid: PEI and/or plasmid: PEI is in the range of about 1:1 to about 50:1 (N: P).

In a further embodiment, the molar ratio of nitrogen (N) in the Total PEI to phosphate (P) in nucleic acid: PEI and/or plasmid: PEI is about 5:1 to about 10:1.

In a further embodiment, the molar ratio of nitrogen (N) in the Total PEI to phosphate (P) in nucleic acid: PEI and/or plasmid: PEI is any of about 5:1, 6:1, 7:1, 8:1, 9:1, or 10:1 (N: P).

In a further embodiment, the amount of Free PEI is about 10% to about 90% of the Total PEI.

In a further embodiment, the amount of Free PEI is about 25% to about 75% of the Total PEI.

In a further embodiment, the amount of Free PEI is about 50% of the Total PEI.

In a further embodiment, the amount of Free PEI is about 0.1 µg/mL to about 10 µg/mL.

In a further embodiment, the amount of Free PEI is about 1.0 µg/mL to about 5 µg/mL.

In a further embodiment, the PEI solution and/or Free PEI comprises a solution having a pH from about 7.0 to about 8.0.

In a further embodiment, the nucleic acid sequence and PEI have been incubated from about 10 seconds to about 4 hours with each other prior to step (a).

In a further embodiment, nucleic acid sequence and PEI have been incubated from about 30 seconds to about 4 hours with each other prior to step (a).

In a further embodiment, the nucleic acid sequence and PEI have been incubated from about 1 minute to about 30 minutes with each other prior to step (a).

In a further embodiment, the mixture of components (i), (ii) and (iii) are incubated together for about 10 seconds to about 4 hours prior to step (b).

In a further embodiment, the mixture of components (i), (ii) and (iii) are incubated together for about 30 seconds to about 4 hours prior to step (b).

In a further embodiment, the mixture of components (i), (ii) and (iii) are incubated together for about 1 minute to about 4 hours prior to step (b).

In a further embodiment, the incubating of step (d) is for at least about 4 hours.

In a further embodiment, the incubating of step (d) is for about 4 hours to about 140 hours.

In a further embodiment, the incubating of step (d) is for about 4 hours to about 96 hours.

In a further embodiment, the cells comprise mammalian cells. In particular aspects, the cells are human embryonic kidney (HEK) or Chinese hamster ovary (CHO) cells. In particular aspects, the cells comprise Human Embryonic Kidney (HEK) 293 cells. In particular aspects, the cells are HEK 293E, HEK 293F or HEK 293T cells.

In a further embodiment, the cells are stably or transiently transfected.

In a further embodiment, the cells are in suspension culture.

In a further embodiment, the cells are adherent.

In a further embodiment, the cells are grown or maintained in a serum-free culture medium.

In a further embodiment, the cells are at a density in the range of about $1 \times 10^5$ cells/mL to about $1 \times 10^8$ cells/mL when contacted with said nucleic acid sequence or said plasmid/PEI mixture and/or when contacted with said Free PEI.

In a further embodiment, the cells are at a density in the range of about $5 \times 10^5$ cells/mL to about $1 \times 10^7$ cells/mL when contacted with said nucleic acid sequence or said plasmid/PEI mixture and/or when contacted with said Free PEI.

In a further embodiment, the cells are at a density in the range of about $1 \times 10^6$ cells/mL to about $5 \times 10^6$ cells/mL when contacted with said nucleic acid sequence or said plasmid/PEI mixture and/or when contacted with said Free PEI.

In a further embodiment, the viability of the cells when contacted with said nucleic acid sequence or plasmid/PEI mixture or with said Free PEI is about 60% or greater than 60%, or wherein said cells are in log phase growth when contacted with said nucleic acid sequence or plasmid/PEI mixture.

In a further embodiment, the viability of the cells when contacted with said nucleic acid sequence or plasmid/PEI mixture or with said Free PEI is about 90% or greater than 90%, or wherein said cells are in log phase growth when contacted with said nucleic acid sequence or plasmid/PEI mixture or with said Free PEI.

In a further embodiment, the total amount of nucleic acid sequence or plasmids is in the range of about 0.1 µg to about 15 µg per mL of cells.

In a further embodiment, the molar ratio of the plasmid comprising the transgene to the one or more plasmids comprising nucleic acids encoding AAV packaging proteins and/or nucleic acids encoding helper proteins is from about 1:5 to about 1:1, or is from about 1:1 to about 5:1.

In a further embodiment, the one or more plasmids comprises a first plasmid comprising the nucleic acids encoding AAV packaging proteins and a second plasmid comprising the nucleic acids encoding helper proteins.

In a further embodiment, the molar ratio of the plasmid comprising the transgene to the first plasmid comprising the nucleic acids encoding AAV packaging proteins to the second plasmid comprising the nucleic acids encoding helper proteins is in the range of about 1-5:1:1, or 1:1-5:1, or 1:1:1-5.

In a further embodiment, the encoded AAV packaging proteins comprise AAV rep and/or AAV cap.

In a further embodiment, the encoded AAV packaging proteins comprise AAV rep and/or AAV cap proteins of any AAV serotype.

In a further embodiment, the encoded helper proteins comprise adenovirus E2 and/or E4, VARNA proteins, and/or non-AAV helper proteins.

In a further embodiment, the recombinant AAV vector comprises any of AAV serotypes 1-12, an AAV VP1, VP2 and/or VP3 capsid protein, or a modified or variant AAV VP1, VP2 and/or VP3 capsid protein, or wild-type AAV VP1, VP2 and/or VP3 capsid protein.

In a further embodiment, the adeno-associated viral (AAV) vector comprises a capsid VP1, VP2 and/or VP3 protein sequence or inverted terminal repeat sequence having 70% or more sequence identity to a capsid protein sequence or to an inverted terminal repeat (ITR) sequence of any capsid protein sequence or ITR selected from AAV1, AAV2, AAV3, AAV4, AAV5, AAV6, AAV7, AAV8, AAV9, and AAV10 serotypes.

In a further embodiment, the adeno-associated viral (AAV) vector comprises a capsid VP1, VP2 and/or VP3 protein sequence having 70% or more sequence identity to a capsid protein sequence selected from SEQ ID NO:1 and SEQ ID NO:2.

In a further embodiment, the AAV vector comprises an AAV serotype or an AAV pseudotype, wherein said AAV pseudotype comprises an AAV capsid serotype different from the ITR serotype.

In a further embodiment, the AAV vector comprises a capsid VP1, VP2 and/or VP3 protein or inverted terminal repeat of any serotype selected from AAV1, AAV2, AAV3, AAV4, AAV5, AAV6, AAV7, AAV8, AAV9, AAV10, SEQ ID NO: 1 and SEQ ID NO:2.

In a further embodiment, the AAV vector further comprises an intron, an expression control element, one or more adeno-associated virus (AAV) inverted terminal repeats (ITRs) and/or a filler polynucleotide sequence.

In a further embodiment, an intron is within or flanks the nucleic acid that encodes a protein or is transcribed into a transcript of interest.

In a further embodiment, an expression control element is operably linked to nucleic acid that encodes a protein or is transcribed into a transcript of interest In a further embodiment, an AAV ITR(s) flanks the 5' or 3' terminus of the nucleic acid that encodes a protein or is transcribed into a transcript of interest.

In a further embodiment, a filler polynucleotide sequence flanks the 5' or 3'terminus of the nucleic acid that encodes a protein or is transcribed into a transcript of interest.

In a further embodiment, the expression control element comprises a constitutive or regulatable control element, or a tissue-specific expression control element or promoter.

In a further embodiment, the expression control element comprises an element that confers expression in liver.

In a further embodiment, an ITR comprises one or more ITRs of any of AAV2 or AAV6 serotypes, or a combination thereof.

In a further embodiment, the cells are subcultured to a reduced cell density prior to contact with said nucleic acid sequence or plasmid/PEI mixture.

In a further embodiment, the cells are subcultured to a cell density in the range of about $0.1 \times 10^6$ cells/mL to about $5.0 \times 10^6$ cells/mL prior to contact with said nucleic acid sequence or plasmid/PEI mixture.

In a further embodiment, the cells are contacted with said nucleic acid sequence or plasmid/PEI mixture between a period of 2 days to 5 days after subculture.

In a further embodiment, the cells are contacted with said nucleic acid sequence or plasmid/PEI mixture between a period of 3 days to 4 days after subculture.

In a further embodiment, the amount of nucleic acid sequence or plasmids introduced into said transfected cells is at least 50% greater with the step of adding Free PEI to the cell culture compared to without adding Free PEI to the cell culture.

In a further embodiment, the amount of nucleic acid sequence or plasmids introduced into said transfected cells is at least 50% greater with the step of adding the enhancing agent compared to without adding the enhancing agent.

In a further embodiment, the amount of recombinant AAV vector produced is at least 50% or greater with the step of adding Free PEI to the plasmid/PEI cell culture compared to without adding Free PEI to the plasmid/PEI cell culture.

In a further embodiment, the amount of recombinant AAV vector produced is 1-5, 5-8, 8-10 or 10-20 fold greater with the step of adding Free PEI to the plasmid/PEI cell culture compared to without adding Free PEI to the plasmid/PEI cell culture.

In a further embodiment, the amount of recombinant AAV vector produced is 1-5, 5-8, 8-10 or 10-15 fold greater with the step of adding the enhancing agent compared to without adding the enhancing agent to the plasmid/PEI cell culture.

In a further embodiment, the cells are in a culture volume of about 10-500 mL, 500 mL-2 Liters, 2-20 Liters, 20-50 Liters, 50-100 Liters, 100-500 Liters, 500-1,000 Liters, or 1,000-2,000 Liters.

In a further embodiment, the transgene has a size from about 4.0 Kb to about 6.0 Kb.

In a further embodiment, the transgene has a size from about 4.5 Kb to about 6.0 Kb.

In a further embodiment, the transgene has a size from about 4.5 Kb to about 5.5 Kb.

In a further embodiment, the transgene has a size from about 4.5 Kb to about 5.0 Kb.

In a further embodiment, the enhancing agent comprises valproic acid, a salt or a derivative thereof. In a particular aspect, a valproic acid salt comprises a sodium or potassium salt. In a particular aspect, a valproic acid derivative comprises an amino acid linked or conjugated thereto.

In a further embodiment, the enhancing agent comprises isobutyric acid, a salt or a derivative thereof. In a particular aspect, an isobutyric acid salt comprises a sodium or potassium salt. In a particular aspect, an isobutyric acid derivative comprises an amino acid linked or conjugated thereto.

In a further embodiment, the enhancing agent comprises isovaleric acid, a salt or a derivative thereof. In a particular aspect, an isovaleric acid salt comprises a sodium or potassium salt. In a particular aspect, an isovaleric acid derivative comprises an amino acid linked or conjugated thereto.

In a further embodiment, after addition the enhancing agent(s) is at a concentration from about 0.1 mM to about 25 mM.

In a further embodiment, after addition the enhancing agent(s) is at a concentration from about 0.5 mM to about 10 mM.

In a further embodiment, after addition the enhancing agent(s) is at a concentration from about 0.5 mM to about 5 mM.

In further embodiments, after addition the enhancing agent(s) is at a concentration from about 1 mM to about 10 mM, from about 1 mM to about 9 mM, from about 1 mM to about 8 mM, from about 1 mM to about 7 mM, from about 1 mM to about 6 mM, from about 1 mM to about 5 mM, from about 1 mM to about 4 mM, from about 1 mM to about 3 mM, or from about 1 mM to about 2 mM.

In further embodiments, any of steps (a)-(f) are performed as set forth in any of Examples 1-3.

DETAILED DESCRIPTION

Figure 1:
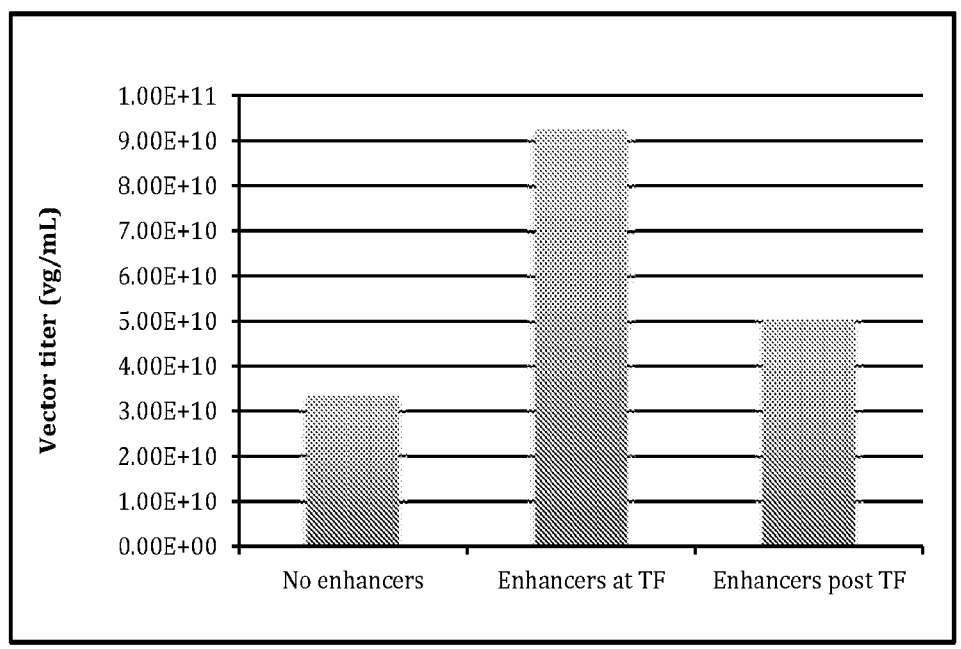
FIG. 1 shows a comparison of rAAV-FVIII vector productivity. HEK 293F cells in spinner flasks were transfected with three plasmids: pAd helper plasmid containing helper genes from adenovirus for rAAV production; pAAV rep/cap express AAV genes of Reps and Caps; pAAVhFVIII containing human Factor VIII expression cassette flanked by AAV ITRs. Total DNA amount used was 1.86 µg/mL with molar ratio of 1:1:1. PEI/DNA ratio of 1:1 (weight) was used to prepare the PEI/DNA complex and transfect cells. Additional free PEI (same amount as used to prepare the PEI/DNA complex) was also added to the cell culture separately at transfection. Enhancers 1 and 2 from the Expi-Fectamine™ 293 Transfection Kit were added to cells either simultaneously at transfection or 16-18 hr post-transfection (as instructed by the manufacturer). Enhancer 1 and 2 were used at 1:200 and 1:20 of culture volume, respectively. The cell culture was harvested at 72 hr post transfection and rAAV-FVIII vector determined by Q-PCR analysis. rAAV-FVIII vector titer was 2-3 fold higher when the enhancers were added at the time of transfection compared to addition of the enhancers 16 hours post-transfection or without the addition of enhancers.

Disclosed herein are compositions and methods of transducing cells with a molecule, such as a nucleic acid (e.g., plasmid), at high efficiency. Such high efficiency transduced cells can, when transduced with a nucleic acid (plasmid) that encodes a protein or comprises a sequence that is transcribed into a transcript of interest, can produce protein and/or transcript at high efficiency. Additionally, such cells when transduced with sequences, such as plasmids that encode viral packaging proteins and/or helper proteins and a transgene that encodes a protein or is transcribed into a transcript of interest, can produce recombinant vectors that include the transgene that encodes a protein or comprises a sequence that is transcribed into a transcript of interest, which in turn produces recombinant viral vectors at high yield.

The invention provides a cell transfection/transduction and/or a viral (e.g., AAV) vector production platform that includes features that distinguish it from current 'industry-standard' viral (e.g., AAV) vector production processes. The compositions and methods of the invention are characterized by mixing PEI with nucleic acids under certain conditions. Mixing PEI with nucleic acids results in PEI-induced efficient compaction of nucleic acids to form stable complexes termed polyplexes. The compositions and methods of transfecting cells with nucleic acids comprises contacting cells with nucleic acid mixed with PEI under certain conditions.

The compositions and methods of the invention further include adding an enhancing agent to the cells. In certain embodiments, an enhancing agent is added prior to, or at about or at the same time, as cells are contacted with the nucleic acid/PEI mix. In certain embodiments, an enhancing agent is added after contacting cells with the nucleic acid/PEI mix. In certain aspects, an enhancing agent is added 5-30 or 30-60 seconds after contacting cells with the nucleic acid/PEI mix. In certain aspects, an enhancing agent is added 1-2, 2-5, 5-10, 10-20, 20-30, 30-60 minutes after contacting cells with the nucleic acid/PEI mix. In certain aspects, an enhancing agent is added 1-2, 2-4, 4-6, 6-12, 12-24, 24-36, 36-48 or 48-72 hours after contacting cells with the nucleic acid/PEI mix.

An enhancing agent can be maintained in contact with cells for a period of time. In certain embodiments, an enhancing agent is in contact with cells for 5 minutes to 72 hours after cells are contacted with the nucleic acid/PEI mix. In certain embodiments, an enhancing agent is in contact with cells for 1-2, 2-5, 5-10, 10-20, 20-30, 30-60 minutes after cells are contacted with the nucleic acid/PEI mix. In certain aspects, an enhancing agent is in contact with cells for 1-72 hours, 6-48 hours, 12-36 hours 24-48 hours or 36-72 hours after cells are contacted with the nucleic acid/PEI mix. In certain aspects, an enhancing agent is in contact with cells for 1-2, 2-4, 4-6, 6-12, 12-24, 24-36, 36-48 or 48-72 hours after cells are contacted with the nucleic acid/PEI mix.

In certain embodiments, cells are contacted with Free PEI, or the methods include contacting cells with Free PEI, in a particular sequence with respect to the step of contacting cells with the PEI/nucleic acid mixture. In certain embodiments, cells are contacted with Free PEI at about or at the same time, as cells are contacted with the nucleic acid/PEI mix. In particular embodiments, cells are contacted with Free PEI after cells have been contacted with the nucleic acid/PEI mixture.

In certain embodiments, cells are contacted with Free PEI, or the methods include contacting cells with Free PEI, in a particular sequence with respect to the step of adding an enhancing agent to the cells contacted with the nucleic acid/PEI mixture. In certain embodiments, cells are contacted with Free PEI at about or at the same time as cells are contacted with an enhancing agent. In particular embodiments, cells are contacted with Free PEI after cells have been contacted with an enhancing agent.

The terms "nucleic acid" and "polynucleotide" are used interchangeably herein to refer to all forms of nucleic acid, oligonucleotides, including deoxyribonucleic acid (DNA) and ribonucleic acid (RNA). Nucleic acids and polynucleotides include genomic DNA, cDNA and antisense DNA, and spliced or unspliced mRNA, rRNA tRNA and inhibitory DNA or RNA (RNAi, e.g., small or short hairpin (sh) RNA, microRNA (miRNA), small or short interfering (si) RNA, trans-splicing RNA, or antisense RNA). Nucleic acids and polynucleotides include naturally occurring, synthetic, and intentionally modified or altered sequences (e.g., variant nucleic acid).

A nucleic acid or plasmid can also refer to a sequence which encodes a protein. Such proteins can be wild-type or a variant, modified or chimeric protein. A "variant protein" can mean a modified protein such that the modified protein has an amino acid alteration compared to wild-type protein.

Proteins encoded by a nucleic acid or plasmid include therapeutic proteins. Non-limiting examples include a blood clotting factor (e.g., Factor XIII, Factor IX, Factor X, Factor VIII, Factor VIIa, or protein C), apoE2, TPP1, argininosuccinate synthase, copper transporting ATPase 2, acid alpha-glucosidase, β-Glucocerebrosidase, α-galactosidase, C1 inhibitor serine protease inhibitor, CFTR (cystic fibrosis transmembrane regulator protein), an antibody, retinal pigment epithelium-specific 65 kDa protein (RPE65), erythropoietin, LDL receptor, lipoprotein lipase, ornithine transcarbamylase, β-globin, α-globin, spectrin, α-antitrypsin, adenosine deaminase (ADA), a metal transporter (ATP7A or ATP7), sulfamidase, an enzyme involved in lysosomal storage disease (ARSA), hypoxanthine guanine phosphoribosyl transferase, β-25 glucocerebrosidase, sphingomyelinase, lysosomal hexosaminidase, branched-chain keto acid dehydrogenase, a hormone, a growth factor (e.g., insulin-like growth factors 1 and 2, platelet derived growth factor, epidermal growth factor, nerve growth factor, neurotrophic factor-3 and -4, brain-derived neurotrophic factor, glial derived growth factor, transforming growth factor α and β, etc.), a cytokine (e.g., α-interferon, β-interferon, interferon-γ, interleukin-2, interleukin-4, interleukin 12, granulocyte-macrophage colony stimulating factor, lymphotoxin, etc.), a suicide gene product (e.g., herpes simplex virus thymidine kinase, cytosine deaminase, diphtheria toxin, cytochrome P450, deoxycytidine kinase, tumor necrosis factor, etc.), a drug resistance protein (e.g., that provides resistance to a drug used in cancer therapy), a tumor suppressor protein (e.g., p53, Rb, Wt-1, NF1, Von Hippel-Lindau (VHL), adenomatous polyposis coli (APC)), a peptide with immunomodulatory properties, a tolerogenic or immunogenic peptide or protein Tregitopes, or hCDR1, insulin, glucokinase, guanylate cyclase 2D (LCA-GUCY2D), Rab escort protein 1 (Choroideremia), LCA 5 (LCA-Lebercilin), ornithine ketoacid aminotransferase (Gyrate Atrophy), Retinoschisin 1 (X-linked Retinoschisis), USHIC (Usher's Syndrome 1C), X-linked retinitis pigmentosa GTPase (XLRP), MERTK (AR forms of RP: retinitis pigmentosa), DFNB1 (Connexin 26 deafness), ACHM 2, 3 and 4 (Achromatopsia), PKD-1 or PKD-2 (Polycystic kidney disease), TPP1, CLN2, gene deficiencies causative of lysosomal storage diseases (e.g., sulfatases, N-acetylglucosamine-1-phosphate transferase, cathepsin A, GM2-AP, NPC1, VPC2, Sphingolipid activator proteins, etc.), one or more zinc finger nucleases for genome editing, or donor sequences used as repair templates for genome editing.

A nucleic acid or plasmid can also refer to a sequence which produces a transcript when transcribed. Such transcripts can be RNA, such as inhibitory RNA (RNAi, e.g., small or short hairpin (sh) RNA, microRNA (miRNA), small or short interfering (si) RNA, trans-splicing RNA, or anti-sense RNA).

Non-limiting examples include inhibitory nucleic acids that inhibit expression of: huntingtin (HTT) gene, a gene associated with dentatorubropallidolusyan atropy (e.g., atrophin 1, ATN1); androgen receptor on the X chromosome in spinobulbar muscular atrophy, human Ataxin-1,-2,-3, and -7, Cav2.1 P/Q voltage-dependent calcium channel is encoded by the (CACNA1A), TATA-binding protein, Ataxin 8 opposite strand, also known as ATXN8OS, Serine/threonine-protein phosphatase 2A 55 kDa regulatory subunit B beta isoform in spinocerebellar ataxia (type 1, 2, 3, 6, 7, 8, 12 17), FMR1 (fragile X mental retardation 1) in fragile X syndrome, FMR1 (fragile X mental retardation 1) in fragile X-associated tremor/ataxia syndrome, FMR1 (fragile X mental retardation 2) or AF4/FMR2 family member 2 in fragile XE mental retardation; Myotonin-protein kinase (MT-PK) in myotonic dystrophy; Frataxin in Friedreich's ataxia; a mutant of superoxide dismutase 1 (SOD1) gene in amyotrophic lateral sclerosis; a gene involved in pathogenesis of Parkinson's disease and/or Alzheimer's disease; apolipoprotein B (APOB) and proprotein convertase subtilisin/kexin type 9 (PCSK9), hypercoloesterolemia; HIV Tat, human immunodeficiency virus transactivator of transcription gene, in HIV infection; HIV TAR, HIV TAR, human immunodeficiency virus transactivator response element gene, in HIV infection; C-C chemokine receptor (CCR5) in HIV infection; Rous sarcoma virus (RSV) nucleocapsid protein in RSV infection, liver-specific microRNA (miR-122) in hepatitis C virus infection; p53, acute kidney injury or delayed graft function kidney transplant or kidney injury acute renal failure; protein kinase N3 (PKN3) in advance recurrent or metastatic solid malignancies; LMP2, LMP2 also known as proteasome subunit beta-type 9 (PSMB 9), metastatic melanoma; LMP7, also known as proteasome subunit beta-type 8 (PSMB 8), metastatic melanoma; MECL1 also known as proteasome subunit beta-type 10 (PSMB 10), metastatic melanoma; vascular endothelial growth factor (VEGF) in solid tumors; kinesin spindle protein in solid tumors, apoptosis suppressor B-cell CLL/lymphoma (BCL-2) in chronic myeloid leukemia; ribonucleotide reductase M2 (RRM2) in solid tumors; Furin in solid tumors; polo-like kinase 1 (PLK1) in liver tumors, diacylglycerol acyltransferase 1 (DGAT1) in hepatitis C infection, beta-catenin in familial adenomatous polyposis; beta2 adrenergic receptor, glaucoma; RTP801/Redd1 also known as DAN damage-inducible transcript 4 protein, in diabetic macular oedma (DME) or age-related macular degeneration; vascular endothelial growth factor receptor I (VEGFR1) in age-related macular degeneration or choroidal neovascularization, caspase 2 in non-arteritic ischaemic optic neuropathy; Keratin 6A N17K mutant protein in pachyonychia congenital; influenza A virus genome/gene sequences in influenza infection; severe acute respiratory syndrome (SARS) coronavirus genome/gene sequences in SARS infection; respiratory syncytial virus genome/gene sequences in respiratory syncytial virus infection; Ebola filovirus genome/gene sequence in Ebola infection; hepatitis B and C virus genome/gene sequences in hepatitis B and C infection; herpes simplex virus (HSV) genome/gene sequences in HSV infection, coxsackievirus B3 genome/gene sequences in coxsackievirus B3 infection; silencing of a pathogenic allele of a gene (allele-specific silencing) like torsin A (TORIA) in primary dystonia, pan-class I and HLA-allele specific in transplant; mutant rhodopsin gene (RHO) in autosomal dominantly inherited retinitis pigmentosa (adRP); or the inhibitory nucleic acid binds to a transcript of any of the foregoing genes or sequences.

Nucleic acids (plasmids) can be single, double, or triplex, linear or circular, and can be of any length. In discussing nucleic acids (plasmids), a sequence or structure of a particular polynucleotide may be described herein according to the convention of providing the sequence in the 5' to 3' direction.

A "plasmid" is a form of nucleic acid or polynucleotide that typically has additional elements for expression (e.g., transcription, replication, etc.) or propagation (replication) of the plasmid. A plasmid as used herein also can be used to reference nucleic acid and polynucleotide sequences. Accordingly, in all aspects the invention compositions and methods are applicable to plasmids, nucleic acids and polynucleotides, e.g., for introducing plasmids, nucleic acid or polynucleotide into cells, for transducing (transfecting) cells with plasmid, nucleic acid or polynucleotide, for producing transduced (transfected) cells that have a plasmid, nucleic acid or polynucleotide, to produce cells that produce viral (e.g., AAV) vectors, to produce viral (e.g., AAV) vectors, to produce cell culture medium that has viral (e.g., AAV) vectors, etc.

Compositions and methods of the invention include polyethyleneimine (PEI). PEI is a cationic polymer and is able to form a stable complex with nucleic acid, referred to as a polyplex. Although not wishing to be bound by any theory, the polyplex is believed to be introduced into cells through endocytosis.

PEI can be linear PEI or branched PEI. PEI can be in a salt form or free base. In particular embodiments, PEI is linear PEI, such as an optionally hydrolyzed linear PEI. The hydrolyzed PEI may be fully or partially hydrolyzed. Hydrolyzed linear PEI has a greater proportion of free (protonatable) nitrogens compared to non-hydrolyzed linear PEI, typically having at least 1-5% more free (protonatable) nitrogens compared to non-hydrolyzed linear PEI, more typically having 5-10% more free (protonatable) nitrogens compared to non-hydrolyzed linear PEI, or most typically having 10-15% more free (protonatable) nitrogens compared to non-hydrolyzed linear PEI.

In particular embodiments, PEI can have a molecular weight in the range of about 4,000 to about 160,000 and/or in the range of about 2,500 to about 250,000 molecular weight in free base form. In further particular embodiments, PEI can have a molecular weight of about 40,000 and/or about 25,000 molecular weight in free base form. Specifically, linear PEI with a molecular weight of about 40,000 and/or about 25,000 molecular weight in free base form. In addition, chemically modified linear PEI or branched PEI can be also used. PEI is commercially available (e.g., Polysciences, Inc., Warrington, PA, USA).

In invention compositions and methods, a nucleic acid, such as a plasmid is mixed with PEI to form a PEI mixture or solution. Such a mixture or solution can be referred to as "a plasmid/PEI mixture," or "a nucleic acid/PEI mixture." The terms "plasmid/PEI mixture" and "nucleic acid/PEI mixture" therefore mean that the PEI has been mixed with the nucleic acid/plasmid. The PEI as set forth herein may therefore be mixed with nucleic acid (plasmid), prior to or substantially simultaneously with contact of the cells for transduction/transfection.

As used herein, the term "Free PEI" means PEI that is substantially or entirely free of nucleic acid (plasmid). The PEI as set forth herein may therefore also be in the form of Free PEI. The "plasmid/PEI mixture" or "nucleic acid/PEI mixture" is therefore distinct from Free PEI. If Free PEI is substantially free, the amount of nucleic acid (plasmid) sequences present, will be no more than about 5% as determined by molecular weight or by mass. Of course, the amount may be less than 5%, e.g., about 4.5% or less, about 4% or less, about 3.5% or less, about 3% or less, about 2.5% or less, about 2% or less, about 1.5% or less, about 1% or less, or about 0.5% or less.

As used herein, the term "Total PEI" means the sum of PEI present in PEI/plasmid mixture and Free PEI. The Total PEI therefore includes PEI that is mixed with the plasmid and PEI that is substantially or entirely free of nucleic acid sequences, such as a plasmid.

The disclosure of PEI quantities, ratios, compositions, solutions, solvents and buffers, pH, salts, and timing and duration of cell contact and incubation applies to any one of, any two of, or all three of: 1) PEI in a plasmid/PEI mixture or in a nucleic acid/PEI mixture; 2) PEI as Free PEI (i.e., PEI that is substantially or entirely free of nucleic acid or polynucleotide sequences, such as a plasmid; and 3) Total PEI (PEI in a plasmid/PEI mixture or in a nucleic acid/PEI mixture+Free PEI).

In particular embodiments, PEI is a solution, such as an aqueous (e.g., water) solutions. In additional particular embodiments, PEI is acidified or neutralized PEI. The term "acidified PEI" means a PEI solution that is prepared by dissolving PEI in an acidic solvent. Acidity of the acidified PEI solution is typically a pH from about 0 to about 3.0, more typically a pH from about 0.5 to about 2.0. The term "neutralized PEI" means a PEI solution that is prepared by dissolving PEI in a neutral solvent or buffer. Neutralized PEI solutions can have a pH in the range of about 6.0 to about 8.0, typically a pH in the range of about 6.5 to about 7.5, more typically a pH in the range of about 6.8 to about 7.2, and most typically a pH in the range of about 7.0 to about 7.2, e.g., about 7.1.

Any solvent or buffer can be used for establishing or maintaining pH of a PEI solution within an aforementioned range without destroying the transfection activity of PEI. Examples of acidic solvents include mineral acids such as Hydrochloric acid (HCl), and organic acids with pH in acidic range such as glycine-hydrochloric acid solution. Non-limiting examples of neutral solvents/buffers include Tris(trizma base) and HEPES. Buffers can range from about 1 mM to about 100 mM, more typically from about 2 mM to about 50 mM, and most typically from about 5 mM to about 20 mM.

PEI solutions can optionally include salts. Non-limiting examples of salts include sodium (Na), potassium (K) and magnesium (Mg) salts. In particular aspects, salt concentrations of a PEI solution ranges from about 50 mM to about 500 mM, more typically from about 100 mM to about 250 mM, and most typically from about 125 mM to about 175 mM.

A mixture of nucleic acids (plasmid) and PEI is carried out by mixing nucleic acids (plasmid) and PEI in a solution. The mixing can occur in any solution compatible with PEI based cell transduction. Non-limiting examples are as set forth herein. After mixing, the nucleic acids (plasmid)/PEI mixture can be incubated for a time period of from about 1 minute to about 8 hours; from about 10 seconds to about 4 hours; from about 1 minute to about 60 minutes; from about 1 minute to about 30 minutes; from about 10 minutes to about 45 minutes; from about 10 minutes to about 30 minutes; and/or from about 20 minutes to about 30 minutes. Typically times include about 1 minute, about 5 minutes, about 10 minutes, about 15 minutes, about 20 minutes and about 30 minutes.

PEI and nucleic acids (plasmid) are mixed at a ratio that is not limited. Typical ratios include a mixture of plasmids in a molar (or weight) ratio range of about 1:0.01 to about 1:100, or in a molar (or weight) ratio range of about 100:1 to about 1:0.01, to produce plasmid/PEI mixture. More typical molar (or weight) ratios include a mixture of plasmids in a molar (or weight) ratio range of about 1:1 to about 1:5, or in a molar (or weight) ratio range of about 1:2 to about 1:4, to produce plasmid/PEI mixture. In additional embodiments, the PEI: plasmid weight ratio is in the range of about 0.1:1 to about 5:1, or in the range of about 5:1 to about 0.1:1. In further embodiments, Free PEI/plasmid/PEI cell culture has a PEI: plasmid weight ratio in the range of about 0.1:1 to about 5:1, or has a PEI: plasmid weight ratio in the range of about 5:1 to about 0.1:1. In particular embodiments, the plasmid/PEI mixture has a PEI: plasmid weight ratio in the range of about 1:1 to about 5:1, or in the range of about 5:1 to about 1:1. In other particular embodiments, the Free PEI/plasmid/PEI cell culture has a PEI: plasmid weight ratio in the range of about 1:1 to about 5:1, or in the range of about 5:1 to about 1:1.

The amount of nucleic acids (plasmid) used to produce compositions and methods of cell transduction varies. In particular embodiments, the molar ratio of nitrogen (N) in Total PEI to phosphate (P) in plasmid is in the range of about 1:1 to about 50:1 (N: P) in the Free PEI/plasmid/PEI cell culture, or the molar ratio of nitrogen (N) in Total PEI to phosphate (P) in plasmid is about 1:1 to 10:1 (N: P) in the Free PEI/plasmid/PEI cell culture, or the molar ratio of nitrogen (N) in Total PEI to phosphate (P) in plasmid is about 5:1, 6:1, 7:1, 8:1, 9:1, or 10:1 (N: P) in the Free PEI/plasmid/PEI cell culture. In additional particular embodiments, the total amount of plasmid comprising the nucleic acid that encodes a protein or is transcribed into a transcript of interest and the one or more plasmids comprising nucleic acids encoding AAV packaging proteins and/or nucleic acids encoding helper proteins is in the range of about 0.1 µg to about 15 µg per mL of cells.

Applying a mixture of nucleic acids (plasmid)/PEI to cells is carried out by adding the nucleic acids (plasmid)/PEI mixture to cells such that the mixture of nucleic acids (plasmid)/PEI contacts the cells. Cells to which the mixture of nucleic acids (plasmid)/PEI solutions is added (contacted) can be adherent cells or cells in suspension. Such cells can include co-cultures with other cells.

Cells are contacted for a time period with a mixture of nucleic acids (plasmid)/PEI that is not limited, to achieve cell transduction. Contact of cells with Free PEI typically occurs concurrently with (or immediately after), or after cells have been contacted with the nucleic acids (plasmid)/PEI mixture. Should there be a time interval between contact of cells with nucleic acids (plasmid)/PEI mixture and contact of the cells with Free PEI, the time interval can be from about 1 second to about 140 hours, typically from about 1 second to about 96 hours, more typically from about 1 second to about 48 or about 72 hours, most typically from about 1 second to about 24 hours, or less, e.g., about 16, about 12, about 8, or about 6 hours, or less.

For long term contact, cells may be affected by cytotoxicity of PEI resulting in an increased amount of dead (non-viable) cells thereby reducing transfection efficiency. The incubation time after cells are contacted with Total PEI can range from seconds to days. Specifically, cells can be contacted with nucleic acids (plasmid)/PEI, or Total PEI, for example, for a time period of from about 1 minute to about 48 hours; from about 1 minute to about 24 hours; from about 1 minute to about 16 hours; from about 1 minute to about 8 hours; from about 1 minute to about 4 hours; from about 1 minute to about 120 minutes; from about 5 minutes to about 60 minutes; from about 10 minutes to about 45 minutes; or from about 10 minutes to about 30 minutes.

To reduce cytotoxicity of PEI, culture medium may be replaced with fresh culture medium after contacting the cells with nucleic acids (plasmid)/PEI. Culture medium replacement after transfection can minimize PEI cytotoxicity without significant loss of cell transfection efficiency.

Cells for transfection, either prior to or at the time of contact with plasmid/PEI mixture, and/or contact with enhancing agent, and/or contact with Free PEI, have a density in the range of about $1 \times 10^5$ cells/mL to about $1 \times 10^8$ cells/mL. Typically, cells have a density in the range of about $2 \times 10^5$ cells/mL to about $5 \times 10^6$ cells/mL. More typically, cells have a density in the range of about $3 \times 10^5$ cells/mL to about $4 \times 10^6$ cells/mL, e.g., about $4 \times 10^5$ cells/mL to about $3 \times 10^6$ cells/mL, or about $5 \times 10^5$ cells/mL to about $2 \times 10^6$ cells/mL. In other embodiments, cells have a density in the range of about $5 \times 10^5$ cells/mL to about $5 \times 10^6$ cells/mL, e.g., about $6 \times 10^5$ cells/mL to about $4 \times 10^6$ cells/mL, or about $7 \times 10^5$ cells/mL to about $3 \times 10^6$ cells/mL. In further embodiments, cells have a density in the range of about $1 \times 10^6$ cells/mL to about $5 \times 10^6$ cells/mL, e.g., about $1 \times 10^6$ cells/mL to about $4 \times 10^6$ cells/mL, or about $2 \times 10^6$ cells/mL to about $3 \times 10^6$ cells/mL.

Cells for transfection, either prior to or at the time of contact with plasmid/PEI mixture, and/or contact with enhancing agent, and/or contact with Free PEI, can optionally be in log (exponential) phase of growth. Cells for transfection, either prior to or at the time of contact with plasmid/PEI mixture, and/or contact with enhancing agent, and/or contact with Free PEI, can optionally have 60% or greater than 60% viability, e.g., 70%, 80%, or 90% or greater than 90% viability.

Cells that may be contacted as set forth herein include mammalian cells, such as human cells. Such cells may be primary cells or cell lines that are capable of growth or maintaining viability in vitro, or have been adapted for in vitro tissue culture. Examples of cell lines include HEK (human embryonic kidney) cells, which include HEK293 cells, such as HEK293F (293F) and HEK293T (293T) cells.

More generally, such cells contacted as set forth herein can be referred to as "host cells." A "host cell" denotes, for example, microorganisms, yeast cells, insect cells, and mammalian cells, that can be, or have been, used as recipients of nucleic acid (plasmid) encoding packaging proteins, such as AAV packaging proteins, a nucleic acid (plasmid) encoding helper proteins, a nucleic acid (plasmid) that encodes a protein or is transcribed into a transcript of interest, or other transfer nucleic acid (plasmid). The term includes the progeny of the original cell, which has been transduced or transfected. Thus, a "host cell" as used herein generally refers to a cell which has been transduced or transfected with an exogenous nucleic acid sequence. It is understood that the progeny of a single parental cell may not necessarily be completely identical in morphology or in genomic or total nucleic acid complement as the original parent, due to natural, accidental, or deliberate mutation.

Numerous cell growth medium appropriate for sustaining cell viability or providing cell growth and/or proliferation are commercially available or can be readily produced. Examples of such medium include serum free eukaryotic growth mediums, such as medium for sustaining viability or providing for the growth of mammalian (e.g., human) cells. Non-limiting examples include Ham's F12 or F12K medium (Sigma-Aldrich), FrecStyle™ (FS) F17 medium (Thermo-Fisher Scientific), MEM, DMEM, RPMI-1640 (Thermo-Fisher Scientific) and mixtures thereof. Such medium can be supplemented with vitamins and/or trace minerals and/or salts and/or amino acids, such as essential amino acids for mammalian (e.g., human) cells.

"Enhancing agents," otherwise referred to herein as "transfection enhancers" or in the same context simply "enhancers" are compounds that increase cell transduction/transfection with a nucleic acid (plasmid). In particular embodiments, an enhancing agent comprises or consists of valproic acid, a salt or a derivative thereof. In certain embodiments, a valproic acid salt comprises or consists of a sodium or potassium salt. In certain embodiments, a valproic acid derivative comprises or consists of an amino acid linked or conjugated thereto. Further examples of enhancing agents include, for example and without limitation, those described in US Patent Publication Nos. 2013/0316400 and 2017/0016043, hereby incorporated by reference in their entirety, as well as other transfection enhancers known in the art.

Enhancing agents, including valproic acid, may be used at a concentration, for example, and without limitation, in the range of about 0.1 mM to about 25 mM, or any sub-ranges or concentration values encompassed thereby. In certain embodiments, a concentration of an enhancing agent is from about 0.5 mM to about 10 mM. In certain embodiments, a concentration of an enhancing agent is from about 0.5 mM to about 5 mM. In certain embodiments, a concentration of an enhancing agent is from about 1 mM to about 4 mM, from about 1 mM to about 3 mM, or from about 1 mM to about 2 mM.

The terms "transduce" and "transfect" refer to introduction of a molecule such as a nucleic acid (plasmid) into a host cell. A cell has been "transduced" or "transfected" when exogenous nucleic acid has been introduced inside the cell membrane. Accordingly, a "transduced cell" is a cell into which a "nucleic acid" or "polynucleotide" has been introduced, or a progeny thereof in which an exogenous nucleic acid has been introduced. In particular embodiments, a "transduced" cell (e.g., in a mammal, such as a cell or tissue or organ cell) is a genetic change in a cell following incorporation of an exogenous molecule, for example, a nucleic acid (e.g., a transgene). A "transduced" or "transfected" cell(s) can be propagated and the introduced nucleic acid transcribed and/or protein expressed.

In a "transduced" or "transfected" cell, the nucleic acid (plasmid) may or may not be integrated into genomic nucleic acid of the recipient cell. If an introduced nucleic acid becomes integrated into the nucleic acid (genomic DNA) of the recipient cell or organism it can be stably maintained in that cell or organism and further passed on to or inherited by progeny cells or organisms of the recipient cell or organism. Finally, the introduced nucleic acid may exist in the recipient cell or host organism extrachromosomally, or only transiently. A number of techniques are known (See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous DNA moieties into suitable host cells.

The term "vector" refers to small carrier nucleic acid molecule, a plasmid, virus (e.g., AAV vector), or other vehicle that can be manipulated by insertion or incorporation of a nucleic acid. Such vectors can be used for genetic manipulation (i.e., "cloning vectors"), to introduce/transfer polynucleotides into cells, and to transcribe or translate the inserted polynucleotide in cells. An "expression vector" is a specialized vector that contains a gene or nucleic acid sequence with the necessary regulatory regions needed for expression in a host cell. A vector nucleic acid sequence generally contains at least an origin of replication for propagation in a cell and optionally additional elements, such as a heterologous polynucleotide sequence, expression control element (e.g., a promoter, enhancer), intron, ITR(s), selectable marker (e.g., antibiotic resistance), polyadenylation signal. For purposes of the invention, a "vector" as set forth herein is within the scope of a "plasmid" as this term is used herein.

A viral vector is derived from or based upon one or more nucleic acid elements that comprise a viral genome. Particular viral vectors include lentivirus, pseudo-typed lentivirus and parvo-virus vectors, such as adeno-associated virus (AAV) vectors.

The term "recombinant," as a modifier of vector, such as recombinant viral, e.g., lenti- or parvo-virus (e.g., AAV) vectors, as well as a modifier of sequences such as recombinant polynucleotides and polypeptides, means that the compositions have been manipulated (i.e., engineered) in a fashion that generally does not occur in nature. A particular example of a recombinant vector, such as an AAV vector would be where a polynucleotide that is not normally present in the wild-type viral (e.g., AAV) genome is inserted within the viral genome, i.e., is heterologous. Although the term "recombinant" is not always used herein in reference to vectors, such as viral and AAV vectors, as well as sequences such as polynucleotides, recombinant forms including polynucleotides, are expressly included in spite of any such omission.

A recombinant viral "vector" or "AAV vector" is derived from the wild type genome of a virus, such as AAV by using molecular methods to remove the wild type genome from the virus (e.g., AAV), and replacing with a non-native nucleic acid, such as a nucleic acid transcribed into a transcript or that encodes a protein. Typically, for AAV one or both inverted terminal repeat (ITR) sequences of AAV genome are retained in the AAV vector. A "recombinant" viral vector (e.g., AAV) is distinguished from a viral (e.g., AAV) genome, since all or a part of the viral genome has been replaced with a non-native (i.e., heterologous) sequence with respect to the viral (e.g., AAV) genomic nucleic acid. Incorporation of a non-native sequence therefore defines the viral vector (e.g., AAV) as a "recombinant" vector, which in the case of AAV can be referred to as a "rAAV vector."

A recombinant vector (e.g., lenti-, parvo-, AAV) sequence can be packaged-referred to herein as a "particle" for subsequent infection (transduction) of a cell, ex vivo, in vitro or in vivo. Where a recombinant vector sequence is encapsidated or packaged into an AAV particle, the particle can also be referred to as a "rAAV." Such particles include proteins that encapsidate or package the vector genome. Particular examples include viral envelope proteins, and in the case of AAV, capsid proteins, such as AAV VP1, VP2 and VP3.

A vector "genome" refers to the portion of the recombinant plasmid sequence that is ultimately packaged or encapsidated to form a viral (e.g., AAV) particle. In cases where recombinant plasmids are used to construct or manufacture recombinant vectors, the vector genome does not include the portion of the "plasmid" that does not correspond to the vector genome sequence of the recombinant plasmid. This non vector genome portion of the recombinant plasmid is referred to as the "plasmid backbone," which is important for cloning and amplification of the plasmid, a process that is needed for propagation and recombinant virus production, but is not itself packaged or encapsidated into virus (e.g., AAV) particles. Thus, a vector "genome" refers to the nucleic acid that is packaged or encapsidated by virus (e.g., AAV).

The terms "empty capsid" and "empty particle," refer to an AAV virion that includes an AAV protein shell but that lacks in whole or part a nucleic acid that encodes a protein or is transcribed into a transcript of interest flanked by AAV ITRs. Accordingly, the empty capsid does not function to transfer a nucleic acid that encodes a protein or is transcribed into a transcript of interest into the host cell. However, empty capsid formulations have utility in other applications, such as ELISA.

The term "packaging proteins" refers to non-AAV derived viral and/or cellular functions upon which AAV is dependent for its replication. Thus, the term captures proteins and RNAs that are required in AAV replication, including those moieties involved in activation of AAV gene transcription, stage specific AAV mRNA splicing, AAV DNA replication, synthesis of Cap expression products and AAV capsid assembly. Viral-based accessory functions can be derived from any of the known helper viruses such as adenovirus, herpesvirus (other than herpes simplex virus type-1) and vaccinia virus.

As used herein, "AAV packaging proteins" refer to AAV-derived sequences which function in trans for productive AAV replication. Thus, AAV packaging proteins are encoded by the major AAV open reading frames (ORFs), rep and cap. The rep proteins have been shown to possess many functions, including, among others: recognition, binding and nicking of the AAV origin of DNA replication; DNA helicase activity; and modulation of transcription from AAV (or other heterologous) promoters. The cap (capsid) proteins supply necessary packaging functions. AAV packaging proteins are used herein to complement AAV functions in trans that are missing from AAV vectors.

The "nucleic acids encoding AAV packaging proteins" refer generally to a nucleic acid molecule that includes nucleotide sequences providing AAV functions deleted from an AAV vector which is to be used to produce a transducing recombinant AAV vector. The nucleic acids encoding AAV packaging proteins are commonly used to provide transient expression of AAV rep and/or cap genes to complement missing AAV functions that are necessary for AAV replication; however, the nucleic acid constructs lack AAV ITRs and can neither replicate nor package themselves. Nucleic acids encoding AAV packaging proteins can be in the form of a plasmid, phage, transposon, cosmid, virus, or virion. A number of nucleic acid constructs have been described, such as the commonly used plasmids pAAV/Ad and pIM29+45 which encode both Rep and Cap expression products. See, e.g., Samulski et al. (1989) J. Virol. 63:3822-3828; and McCarty et al. (1991) J. Virol. 65:2936-2945. A number of vectors have been described which encode Rep and/or Cap expression products (e.g., U.S. Pat. Nos. 5,139,941 and 6,376,237).

The term "nucleic acids encoding helper proteins" refers generally to a nucleic acid molecule(s) that includes nucleotide sequences encoding proteins that provide helper function(s). A vector with nucleic acid(s) encoding helper protein(s) can be transfected into a suitable host cell, wherein the vector is then capable of supporting AAV virion production in the host cell. Expressly excluded from the term are infectious viral particles, as they exist in nature, such as adenovirus, herpesvirus or vaccinia virus particles.

Thus, helper protein vectors can be in the form of a plasmid, phage, transposon or cosmid. In particular, it has been demonstrated that the full-complement of adenovirus genes are not required for helper functions. For example, adenovirus mutants incapable of DNA replication and late gene synthesis have been shown to be permissive for AAV replication. Ito et al., (1970) J. Gen. Virol. 9:243; Ishibashi et al, (1971) Virology 45:317.

Mutants within the E2B and E3 regions have been shown to support AAV replication, indicating that the E2B and E3 regions are probably not involved in providing helper function. Carter et al:, (1983) Virology 126:505. However, adenoviruses defective in the E1 region, or having a deleted E4 region, are unable to support AAV replication. Thus, for adenoviral helper proteins, EIA and E4 regions are likely required for AAV replication, either directly or indirectly. Laughlin et al., (1982) J. Virol. 41:868; Janik et al., (1981) Proc. Natl. Acad. Sci. USA 78:1925; Carter et al., (1983) Virology 126:505. Other characterized Ad mutants include: EIB (Laughlin et al. (1982), supra; Janik et al. (1981), supra; Ostrove et al., (1980) Virology 104:502); E2A (Handa et al., (1975) J. Gen. Virol. 29:239; Strauss et al., (1976) J. Virol. 17:140; Myers et al., (1980) J. Virol. 35:665; Jay et al., (1981) Proc. Natl. Acad. Sci. USA 78:2927; Myers et al., (1981) J. Biol. Chem. 256:567); E2B (Carter, Adeno-Associated Virus Helper Functions, in I CRC Handbook of Parvoviruses (P. Tijssen ed., 1990)); E3 (Carter et al. (1983), supra); and E4 (Carter et al. (1983), supra; Carter (1995)).

Studies of the helper proteins provided by adenoviruses having mutations in the E1B have reported that E1 B55k is required for AAV virion production, while E1B 19k is not. In addition, International Publication WO 97/17458 and Matshushita et al., (1998) Gene Therapy 5:938-945, describe helper function vectors encoding various Ad genes. An example of a helper vector comprise an adenovirus VA RNA coding region, an adenovirus E4 ORF6 coding region, an adenovirus E2A 72 kD coding region, an adenovirus ElA coding region, and an adenovirus E1B region lacking an intact E I BS5k coding region (see, e.g., International Publication No. WO 01/83797).

A "transgene" is used herein to conveniently refer to a nucleic acid that is intended or has been introduced into a cell or organism. Transgenes include any nucleic acid, such as a gene that is transcribed into a transcript or that encodes a polypeptide or protein.

An "expression control element" refers to nucleic acid sequence(s) that influence expression of an operably linked nucleic acid. Control elements, including expression control elements as set forth herein such as promoters and enhancers, Vector sequences including AAV vectors can include one or more "expression control elements." Typically, such elements are included to facilitate proper heterologous polynucleotide transcription and if appropriate translation (e.g., a promoter, enhancer, splicing signal for introns, maintenance of the correct reading frame of the gene to permit in-frame translation of mRNA and, stop codons etc.). Such elements typically act in cis, referred to as a "cis acting" element, but may also act in trans.

Expression control can be at the level of transcription, translation, splicing, message stability, etc. Typically, an expression control element that modulates transcription is juxtaposed near the 5' end (i.e., "upstream") of a transcribed nucleic acid. Expression control elements can also be located at the 3' end (i.e., "downstream") of the transcribed sequence or within the transcript (e.g., in an intron). Expression control elements can be located adjacent to or at a distance away from the transcribed sequence (e.g., 1-10, 10-25, 25-50, 50-100, 100 to 500, or more nucleotides from the polynucleotide), even at considerable distances. Nevertheless, owing to the length limitations of certain vectors, such as AAV vectors, expression control elements will typically be within 1 to 1000 nucleotides from the transcribed nucleic acid.

Functionally, expression of operably linked nucleic acid is at least in part controllable by the element (e.g., promoter) such that the element modulates transcription of the nucleic acid and, as appropriate, translation of the transcript. A specific example of an expression control element is a promoter, which is usually located 5' of the transcribed sequence. A promoter typically increases an amount expressed from operably linked nucleic acid as compared to an amount expressed when no promoter exists.

An "enhancer" as used herein can refer to a sequence that is located adjacent to the heterologous polynucleotide. Enhancer elements are typically located upstream of a promoter element but also function and can be located downstream of or within a nucleic acid sequence. Hence, an enhancer element can be located 100 base pairs, 200 base pairs, or 300 or more base pairs upstream or downstream of a nucleic acid. Enhancer elements typically increase expressed of an operably linked nucleic acid above expression afforded by a promoter element.

An expression construct may comprise regulatory elements which serve to drive expression in a particular cell or tissue type. Expression control elements (e.g., promoters) include those active in a particular tissue or cell type, referred to herein as a "tissue-specific expression control elements/promoters." Tissue-specific expression control elements are typically active in specific cell or tissue (e.g., liver). Expression control elements are typically active in particular cells, tissues or organs because they are recognized by transcriptional activator proteins, or other regulators of transcription, that are unique to a specific cell, tissue or organ type. Such regulatory elements are known to those of skill in the art (see, e.g., Sambrook et al. (1989) and Ausubel et al. (1992)).

The incorporation of tissue specific regulatory elements in the plasmids of the invention provides for at least partial tissue tropism for expression of the nucleic acid. Examples of promoters that are active in liver are the TTR promoter (e.g. mutant TTR promoter), human alpha 1-antitrypsin (hAAT) promoter; albumin, Miyatake, et al. J. Virol., 71:5124-32 (1997); hepatitis B virus core promoter, Sandig, et al., Gene Ther. 3:1002-9 (1996); alpha-fetoprotein (AFP), Arbuthnot, et al., Hum. Gene. Ther., 7:1503-14 (1996)], among others. An example of an enhancer active in liver is apolipoprotein E (apoE) HCR-1 and HCR-2 (Allan et al., J. Biol. Chem., 272:29113-19 (1997)).

Expression control elements also include ubiquitous or promiscuous promoters/enhancers which are capable of driving expression of a polynucleotide in many different cell types. Such elements include, but are not limited to the cytomegalovirus (CMV) immediate early promoter/enhancer sequences, the Rous sarcoma virus (RSV) promoter/enhancer sequences and the other viral promoters/enhancers active in a variety of mammalian cell types, or synthetic elements that are not present in nature (see, e.g., Boshart et al, Cell, 41:521-530 (1985)), the SV40 promoter, the dihydrofolate reductase promoter, the cytoplasmic β-actin promoter and the phosphoglycerol kinase (PGK) promoter.

Expression control elements also can confer expression in a manner that is regulatable, that is, a signal or stimuli increases or decreases expression of the operably linked heterologous polynucleotide. A regulatable element that increases expression of the operably linked polynucleotide in response to a signal or stimuli is also referred to as an "inducible element" (i.e., is induced by a signal). Particular examples include, but are not limited to, a hormone (e.g., steroid) inducible promoter. Typically, the amount of increase or decrease conferred by such elements is proportional to the amount of signal or stimuli present; the greater the amount of signal or stimuli, the greater the increase or decrease in expression. Particular non-limiting examples include zinc-inducible sheep metallothionine (MT) promoter; the steroid hormone-inducible mouse mammary tumor virus (MMTV) promoter; the T7 polymerase promoter system (WO 98/10088); the tetracycline-repressible system (Gossen, et al., Proc. Natl. Acad. Sci. USA, 89:5547-5551 (1992)); the tetracycline-inducible system (Gossen, et al., Science. 268:1766-1769 (1995); see also Harvey, et al., Curr. Opin. Chem. Biol. 2:512-518 (1998)); the RU486-inducible system (Wang, et al., Nat. Biotech. 15:239-243 (1997) and Wang, et al., Gene Ther. 4:432-441 (1997)]; and the rapamycin-inducible system (Magari, et al., J. Clin. Invest. 100:2865-2872 (1997); Rivera, et al., Nat. Medicine. 2:1028-1032 (1996)). Other regulatable control elements which may be useful in this context are those which are regulated by a specific physiological state, e.g., temperature, acute phase, development.

Expression control elements also include the native elements(s) for the nucleic acid. A native control element (e.g., promoter) may be used when it is desired that expression of the heterologous polynucleotide should mimic the native expression. The native element may be used when expression of the heterologous polynucleotide is to be regulated temporally or developmentally, or in a tissue-specific manner, or in response to specific transcriptional stimuli. Other native expression control elements, such as introns, polyadenylation sites or Kozak consensus sequences may also be used.

The term "operably linked" means that the regulatory sequences necessary for expression of a coding sequence are placed in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

In the example of an expression control element in operable linkage with a nucleic acid, the relationship is such that the control element modulates expression of the nucleic acid. More specifically, for example, two DNA sequences operably linked means that the two DNAs are arranged (cis or trans) in such a relationship that at least one of the DNA sequences is able to exert a physiological effect upon the other sequence.

Accordingly, additional elements for vectors include, without limitation, an expression control (e.g., promoter/enhancer) element, a transcription termination signal or stop codon, 5' or 3' untranslated regions (e.g., polyadenylation (polyA) sequences) which flank a sequence, such as one or more copies of an AAV ITR sequence, or an intron.

Further elements include, for example, filler or stuffer polynucleotide sequences, for example to improve packaging and reduce the presence of contaminating nucleic acid. AAV vectors typically accept inserts of DNA having a size range which is generally about 4 kb to about 5.2 kb, or slightly more. Thus, for shorter sequences, inclusion of a stuffer or filler in order to adjust the length to near or at the normal size of the virus genomic sequence acceptable for AAV vector packaging into virus particle. In various embodiments, a filler/stuffer nucleic acid sequence is an untranslated (non-protein encoding) segment of nucleic acid. For a nucleic acid sequence less than 4.7 Kb, the filler or stuffer polynucleotide sequence has a length that when combined (e.g., inserted into a vector) with the sequence has a total length between about 3.0-5.5 Kb, or between about 4.0-5.0 Kb, or between about 4.3-4.8 Kb.

An intron can also function as a filler or stuffer polynucleotide sequence in order to achieve a length for AAV vector packaging into a virus particle. Introns and intron fragments that function as a filler or stuffer polynucleotide sequence also can enhance expression.

The "polypeptides," "proteins" and "peptides" encoded by the "nucleic acid" or "plasmids," include full-length native sequences, as with naturally occurring wild-type proteins, as well as functional subsequences, modified forms or sequence variants so long as the subsequence, modified form or variant retain some degree of functionality of the native full-length protein. For example, a protein can have a deletion, substitution or addition and retain at least partial function or activity.

The terms "modify" or "variant" and grammatical variations thereof mean that a nucleic acid or polypeptide deviates from a reference sequence. Modified and variant sequences may therefore have substantially the same, greater or less expression, activity or function than a reference sequence, but at least retain partial activity or function of the reference sequence.

Non-limiting examples of modifications include one or more nucleotide or amino acid substitutions (e.g., 1-3, 3-5, 5-10, 10-15, 15-20, 20-25, 25-30, 30-40, 40-50, 50-100, 100-150, 150-200, 200-250, 250-500, 500-750, 750-850 or more nucleotides or residues).

An example of an amino acid modification is a conservative amino acid substitution or a deletion (e.g., subsequences or fragments) of a reference sequence. In particular embodiments, a modified or variant sequence retains at least part of a function or activity of unmodified sequence.

All mammalian and non-mammalian forms of nucleic acids that are transcribed and nucleic acids that encode proteins are included. Thus, the invention includes genes and proteins from non-mammals, mammals other than humans, and humans, which genes and proteins function in a substantially similar manner to human genes and proteins.

Following cell transfection and/or production of recombinant viral (e.g., AAV) vectors as set forth herein, if desired the viral (e.g., rAAV) virions can be collected/harvested from the cells/cell culture and optionally purified and/or isolated from transfected cells using a variety of conventional methods. Such methods include column chromatography, CsCl gradients, and the like. For example, a plurality of column purification steps such as purification over an anion exchange column, an affinity column and/or a cation exchange column can be used. (See, e.g., International Publication No. WO 02/12455 and US Application Publication Nos. 20030207439). Alternatively, or in addition, CsCl gradient steps can be used. (See, e.g., US Application Publication Nos. 20120135515; and 20130072548) Further, if the use of infectious virus is employed to express the packaging and/or helper proteins, residual virus can be inactivated, using various methods. For example, adenovirus can be inactivated by heating to temperatures of approximately 60° C. for, e.g., 20 minutes or more. This treatment effectively inactivates the helper virus since AAV is heat stable while the helper adenovirus is heat labile.

The term "isolated," when used as a modifier of a composition, means that the compositions are made by the hand of man or are separated, completely or at least in part, from their naturally occurring in vivo environment. Generally, isolated compositions are substantially free of one or more materials with which they normally associate with in nature, for example, one or more contaminants such as protein, nucleic acid, lipid, carbohydrate, cell membrane.

With respect to RNA molecules, the term "isolated" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule. Alternatively, this term may refer to a protein which has been sufficiently separated from other proteins with which it would naturally be associated, so as to exist in "substantially pure" form.

The term "isolated" does not exclude combinations produced by the hand of man, for example, a recombinant vector (e.g., rAAV) sequence, or virus particle that packages or encapsidates a vector genome and a pharmaceutical formulation. The term "isolated" also does not exclude alternative physical forms of the composition, such as hybrids/chimeras, multimers/oligomers, modifications (e.g., phosphorylation, glycosylation, lipidation) or derivatized forms, or forms expressed in host cells produced by the hand of man.

The term "substantially pure" refers to a preparation comprising at least 50-60% by weight the compound of interest (e.g., nucleic acid, oligonucleotide, protein, etc.). The preparation can comprise at least 75% by weight, or about 90-99% by weight, of the compound of interest. Purity is measured by methods appropriate for the compound of interest (e.g. chromatographic methods, agarose or polyacrylamide gel electrophoresis, HPLC analysis, and the like).

Nucleic acid molecules, expression vectors (e.g., vector genomes), plasmids, may be prepared by using recombinant DNA technology methods. The availability of nucleotide sequence information enables preparation of isolated nucleic acid molecules by a variety of means. For example, nucleic acids (e.g., plasmids) can be made using various standard cloning, recombinant DNA technology, via cell expression or in vitro translation and chemical synthesis techniques. Purity can be determined through sequencing, gel electrophoresis and the like. For example, nucleic acids can be isolated using hybridization or computer-based database screening techniques. Such techniques include, but are not limited to: (1) hybridization of genomic DNA or cDNA libraries with probes to detect homologous nucleotide sequences; (2) antibody screening to detect polypeptides having shared structural features, for example, using an expression library; (3) polymerase chain reaction (PCR) on genomic DNA or cDNA using primers capable of annealing to a nucleic acid sequence of interest; (4) computer searches of sequence databases for related sequences; and (5) differential screening of a subtracted nucleic acid library.

Nucleic acids may be maintained as DNA in any convenient cloning vector. In one embodiment, nucleic acids are maintained in a plasmid. Alternatively, nucleic acids may be maintained in vector suitable for expression in mammalian cells.

Nucleic acids, plasmids, vectors, expression vectors (e.g., rAAV), and recombinant virus particles, methods and uses permit the treatment of genetic diseases. For deficiency state diseases, gene transfer can be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. The use of site-specific integration of nucleic acid sequences to correct defects is also possible.

Viral vectors such as lenti- and parvo-virus vectors, including AAV serotypes and variants thereof provide a means for delivery of nucleic acid into cells ex vivo, in vitro and in vivo, which encode proteins such that the cells express the encoded protein. AAV are viruses useful as gene therapy vectors as they can penetrate cells and introduce nucleic acid/genetic material so that the nucleic acid/genetic material may be stably maintained in cells. In addition, these viruses can introduce nucleic acid/genetic material into specific sites, for example. Because AAV are not associated with pathogenic disease in humans, AAV vectors are able to deliver heterologous polynucleotide sequences (e.g., therapeutic proteins and agents) to human patients without causing substantial AAV pathogenesis or disease.

Viral vectors which may be used include, but are not limited to, adeno-associated virus (AAV) vectors of multiple serotypes (e.g., AAV-1 to AAV-12, and others) and hybrid/chimeric AAV vectors, lentivirus vectors and pseudo-typed lentivirus vectors (e.g., Ebola virus, vesicular stomatitis virus (VSV), and feline immunodeficiency virus (FIV)), herpes simplex virus vectors, adenoviral vectors (with or without tissue specific promoters/enhancers), vaccinia virus vectors, retroviral vectors, lentiviral vectors, non-viral vectors and others.

AAV and lentiviral particles may be used to advantage as vehicles for effective gene delivery. Such virions possess a number of desirable features for such applications, including tropism for dividing and non-dividing cells. Early clinical experience with these vectors also demonstrated no sustained toxicity and immune responses were minimal or undetectable. AAV are known to infect a wide variety of cell types in vivo and in vitro by receptor-mediated endocytosis or by transcytosis. These vector systems have been tested in humans targeting retinal epithelium, liver, skeletal muscle, airways, brain, joints and hematopoietic stem cells. Non-viral vectors, for example, based on plasmid DNA or mini-circles, are also suitable gene transfer vectors.

Accordingly, in various embodiments of the invention a vector includes a lenti- or parvo-viral vector, such as an adeno-viral vector. In particular embodiments, a recombinant vector is a parvovirus vector. Parvoviruses are small viruses with a single-stranded DNA genome. "Adeno-associated viruses" (AAV) are in the parvovirus family.

AAV vectors and lentiviral vectors do not typically include viral genes associated with pathogenesis. Such vectors typically have one or more of the wild type AAV genes deleted in whole or in part, for example, rep and/or cap genes, but retain at least one functional flanking ITR sequence, as necessary for the rescue, replication, and packaging of the recombinant vector into an AAV vector particle. For example, only the essential parts of vector e.g., the ITR and LTR elements, respectively are included. An AAV vector genome would therefore include sequences required in cis for replication and packaging (e.g., functional ITR sequences).

Recombinant AAV vector, as well as methods and uses thereof, include any viral strain or serotype. As a non-limiting example, a recombinant AAV vector can be based upon any AAV genome, such as AAV-1,-2,-3,-4,-5,-6,-7,-8,-9,-10,-11,-12, or AAV-218, for example. Such vectors can be based on the same strain or serotype (or subgroup or variant), or be different from each other. As a non-limiting example, a recombinant AAV vector based upon one serotype genome can be identical to one or more of the capsid proteins that package the vector. In addition, a recombinant AAV vector genome can be based upon an AAV (e.g., AAV2) serotype genome distinct from one or more of the AAV capsid proteins that package the vector. For example, the AAV vector genome can be based upon AAV2, whereas at least one of the three capsid proteins could be a AAV1, AAV3, AAV4, AAV5, AAV6, AAV7, AAV8, AAV9, AAV10, AAV11, AAV12, or AAV-218 or variant thereof, for example. AAV variants include variants and chimeras of AAV1, AAV2, AAV3, AAV4, AAV5, AAV6, AAV7, AAV8, AAV9, AAV10, AAV11, AAV12 AAV-218, SEQ ID NO1 and SEQ ID NO:2 capsids.

In particular embodiments, adeno-associated virus (AAV) vectors include AAV1, AAV2, AAV3, AAV4, AAV5, AAV6, AAV7, AAV8, AAV9, AAV10, AAV11, AAV12, AAV-218, SEQ ID NO1 and SEQ ID NO:2, as well as variants (e.g., capsid variants, such as amino acid insertions, additions, substitutions and deletions) thereof, for example, as set forth in WO 2013/158879 (International Application PCT/US2013/037170), WO 2015/013313 (International Application PCT/US2014/047670) and US 2013/0059732 (U.S. application Ser. No. 13/594,773, discloses LK01, LK02, LK03, etc.).

AAV and AAV variants (e.g., capsid variants) serotypes (e.g., VP1, VP2, and/or VP3 sequences) may or may not be distinct from other AAV serotypes, including, for example, AAV1-AAV12 (e.g., distinct from VP1, VP2, and/or VP3 sequences of any of AAV1-AAV12 serotypes).

As used herein, the term "serotype" is a distinction used to refer to an AAV having a capsid that is serologically distinct from other AAV serotypes. Serologic distinctiveness is determined on the basis of the lack of cross-reactivity between antibodies to one AAV as compared to another AAV. Such cross-reactivity differences are usually due to differences in capsid protein sequences/antigenic determinants (e.g., due to VP1, VP2, and/or VP3 sequence differences of AAV serotypes). Despite the possibility that AAV variants including capsid variants may not be serologically distinct from a reference AAV or other AAV serotype, they differ by at least one nucleotide or amino acid residue compared to the reference or other AAV serotype.

Under the traditional definition, a serotype means that the virus of interest has been tested against serum specific for all existing and characterized serotypes for neutralizing activity and no antibodies have been found that neutralize the virus of interest. As more naturally occurring virus isolates of are discovered and/or capsid mutants generated, there may or may not be serological differences with any of the currently existing serotypes. Thus, in cases where the new virus (e.g., AAV) has no serological difference, this new virus (e.g., AAV) would be a subgroup or variant of the corresponding serotype. In many cases, serology testing for neutralizing activity has yet to be performed on mutant viruses with capsid sequence modifications to determine if they are of another serotype according to the traditional definition of serotype. Accordingly, for the sake of convenience and to avoid repetition, the term "serotype" broadly refers to both serologically distinct viruses (e.g., AAV) as well as viruses (e.g., AAV) that are not serologically distinct that may be within a subgroup or a variant of a given serotype.

In various exemplary embodiments, an AAV vector related to a reference serotype has a polynucleotide, polypeptide or subsequence thereof that includes or consists of a sequence at least 80% or more (e.g., 85%, 90%, 95%, 96%, 97%, 98%, 99%, 99.1%, 99.2%, 99.3%, 99.4%, 99.5%, etc.) identical to one or more AAV1, AAV2, AAV3, AAV4, AAV5, AAV6, AAV7, AAV8, AAV9, AAV10, AAV11, AAV12, AAV-218, SEQ ID NO1 or SEQ ID NO:2 (e.g., such as an ITR, or a VP1, VP2, and/or VP3 sequences).

Compositions, methods and uses of the invention include AAV sequences (polypeptides and nucleotides), and subsequences thereof that exhibit less than 100% sequence identity to a reference AAV serotype such as AAV1, AAV2, AAV3, AAV4, AAV5, AAV6, AAV7, AAV8, AAV9, AAV10, AAV11, AAV12, or AAV-218, but are distinct from and not identical to known AAV genes or proteins, such as AAV1, AAV2, AAV3, AAV4, AAV5, AAV6, AAV7, AAV8, AAV9, AAV10, AAV11, AAV12, or AAV-218, genes or proteins, etc. In one embodiment, an AAV polypeptide or subsequence thereof includes or consists of a sequence at least 75% or more identical, e.g., 80%, 85%, 85%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to any reference AAV sequence or subsequence thereof, such as AAV1, AAV2, AAV3, AAV4, AAV5, AAV6, AAV7, AAV8, AAV9, AAV10, AAV11, AAV12, AAV-218, SEQ ID NO1 or SEQ ID NO:2 (e.g., VP1, VP2 and/or VP3 capsid or ITR). In particular aspects, an AAV variant has 1, 2, 3, 4, 5, 5-10, 10-15, 15-20 or more amino acid substitutions.

Recombinant AAV vectors, including AAV1, AAV2, AAV3, AAV4, AAV5, AAV6, AAV7, AAV8, AAV9, AAV10, AAV11, AAV12, AAV-218, SEQ ID NO1 or SEQ ID NO:2 and variant, related, hybrid and chimeric sequences, can be constructed using recombinant techniques that are known to the skilled artisan, to include one or more nucleic acid sequences (transgenes) flanked with one or more functional AAV ITR sequences.

Nucleic acids (plasmids), vectors, recombinant vectors (e.g., rAAV), and recombinant virus particles can be incorporated into pharmaceutical compositions. Such pharmaceutical compositions are useful for, among other things, administration and delivery to a subject in vivo or ex vivo. In particular embodiments, pharmaceutical compositions contains a pharmaceutically acceptable carrier or excipient. Such excipients include any pharmaceutical agent that does not itself induce an immune response harmful to the individual receiving the composition, and which may be administered without undue toxicity.

As used herein the term "pharmaceutically acceptable" and "physiologically acceptable" mean a biologically acceptable formulation, gaseous, liquid or solid, or mixture thereof, which is suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. Thus, such a pharmaceutical composition may be used, for example in administering a nucleic acid, vector, viral particle or protein to a subject.

Pharmaceutically acceptable excipients include, but are not limited to, liquids such as water, saline, glycerol, sugars and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding, free base forms. In other cases, a preparation may be a lyophilized powder which may contain any or all of the following: 1-50 mM histidine, 0.1%-2% sucrose, and 2-7% mannitol, at a pH range of 4.5 to 5.5, that is combined with buffer prior to use.

Pharmaceutical compositions include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration or delivery. Thus, pharmaceutical compositions include carriers, diluents, or excipients suitable for administration by various routes.

Compositions and methods may be sterile. The compositions may be made and methods may be performed in containers suitable for such processes. Such containers include dishes, flasks, roller bottles, bags, bioreactors, vessels, tubes, vials, etc. Containers may be made of materials that include but are not limited to glass, plastic and polymers, such as polystyrene, polybutylene, polypropylene, etc.

The compositions and method steps may be performed in a designated order, or rearranged order. The method steps can be performed in stages or at intervals with intervening time periods. In other words, a method step can be performed, and then an interval of time between the next step can occur, such intervals ranging, for example, from about 1 second to about 60 seconds; from about 1 minute to about 60 minutes; from about 1 hour to about 24 hours; from about 1 day to about 7 days; or from about 1 week to about 48 weeks.

Protocols for the generation of adenoviral vectors have been described in U.S. Pat. Nos. 5,998,205; 6,228,646; 6,093,699; and 6,100,242; and International Patent Application Nos. WO 94/17810 and WO 94/23744, which are incorporated herein by reference in their entirety.

The invention is useful in producing cells and vectors for human and veterinary medical applications. Suitable subjects therefore include mammals, such as humans, as well as non-human mammals. The term "subject" refers to an animal, typically a mammal, such as humans, non-human primates (apes, gibbons, gorillas, chimpanzees, orangutans, macaques), a domestic animal (dogs and cats), a farm animal (poultry such as chickens and ducks, horses, cows, goats, sheep, pigs), and experimental animals (mouse, rat, rabbit, guinea pig). Human subjects include fetal, neonatal, infant, juvenile and adult subjects. Subjects include animal disease models, for example, mouse and other animal models of blood clotting diseases such as HemA and others known to those of skill in the art.

A "unit dosage form" as used herein refers to physically discrete units suited as unitary dosages for the subject to be treated; each unit containing a predetermined quantity optionally in association with a pharmaceutical carrier (excipient, diluent, vehicle or filling agent) which, when administered in one or more doses, is calculated to produce a desired effect (e.g., prophylactic or therapeutic effect). Unit dosage forms may be within, for example, ampules and vials, which may include a liquid composition, or a composition in a freeze-dried or lyophilized state; a sterile liquid carrier, for example, can be added prior to administration or delivery in vivo. Individual unit dosage forms can be included in multi-dose kits or containers. Recombinant vector (e.g., rAAV) sequences, recombinant virus particles, and pharmaceutical compositions thereof can be packaged in single or multiple unit dosage form for case of administration and uniformity of dosage.

The invention provides kits with packaging material and one or more components therein. A kit typically includes a label or packaging insert including a description of the components or instructions for use of the components therein. A kit can contain a collection of such components, e.g., a nucleic acid (plasmid), PEI, enhancing agent, cells.

A kit refers to a physical structure housing one or more components of the kit. Packaging material can maintain the components sterilely, and can be made of material commonly used for such purposes (e.g., paper, corrugated fiber, glass, plastic, foil, ampules, vials, tubes, etc.).

Labels or inserts can include identifying information of one or more components therein. Labels or inserts can include information identifying manufacturer, lot numbers, manufacture location and date, expiration dates. Labels or inserts can include information identifying manufacturer information, lot numbers, manufacturer location and date. Labels or inserts can include instructions for using one or more of the kit components in a method, use, or manufacturing protocol. Instructions can include instructions for producing the compositions or practicing any of the methods described herein.

Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a bar-coded printed label, a disk, optical disk such as CD- or DVD-ROM/RAM, DVD, MP3, magnetic tape, or an electrical storage media such as RAM and ROM or hybrids of these such as magnetic/optical storage media, FLASH media or memory type cards.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All patents, patent applications, publications, and other references, GenBank citations and ATCC citations cited herein are incorporated by reference in their entirety. In case of conflict, the specification, including definitions, will control.

Various terms relating to the biological molecules of the invention are used hereinabove and also throughout the specification and claims.

All of the features disclosed herein may be combined in any combination. Each feature disclosed in the specification may be replaced by an alternative feature serving a same, equivalent, or similar purpose. Thus, unless expressly stated otherwise, disclosed features (e.g., PEI, plasmid, vector (e.g., rAAV, or recombinant virus particle) are an example of a genus of equivalent or similar features.

As used herein, the singular forms "a", "and," and "the" include plural referents unless the context clearly indicates otherwise. Thus, for example, reference to "a plasmid" or "a nucleic acid" includes a plurality of such plasmids or nucleic acids, reference to "a vector" includes a plurality of such vectors, reference to "a virus" or "particle" includes a plurality of such viruses/particles and reference to an "enhancing agent" includes a plurality of such agents.

As used herein, all numerical values or numerical ranges include integers within such ranges and fractions of the values or the integers within ranges unless the context clearly indicates otherwise. Thus, to illustrate, reference to 80% or more identity, includes 81%, 82%, 83%, 84%, 85%, 86%, 87%, 88%, 89%, 90%, 91%, 92%, 93%, 94%, etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to less than 100, includes 99, 98, 97, etc. all the way down to the number one (1); and less than 10, includes 9, 8, 7, etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-850, includes ranges of 1-20, 1-30, 1-40, 1-50, 1-60, 10-30, 10-40, 10-50, 10-60, 10-70, 10-80, 20-40, 20-50, 20-60, 20-70, 20-80, 20-90, 50-75, 50-100, 50-150, 50-200, 50-250, 100-200, 100-250, 100-300, 100-350, 100-400, 100-500, 150-250, 150-300, 150-350, 150-400, 150-450, 150-500, etc.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless disclosed herein.

A number of embodiments of the invention have been described. Nevertheless, one skilled in the art, without departing from the spirit and scope of the invention, can make various changes and modifications of the invention to adapt it to various usages and conditions. Accordingly, the following examples are intended to illustrate but not limit the scope of the invention claimed in any way.

Example 1

Representative Materials and Methods

Cell Culture: FreeStyle™ 293F (HEK 293F) cells purchased from Thermo Fisher Scientific (R79007) were cultured in FreeStyle™ F17 (F17) expression medium (Thermo Fisher Scientific, A1383501) supplemented with 1× GlutaMAX™ (Thermo Fisher Scientific, 35050-061) and 1× Antibiotic-antimycotic (Thermo Fisher Scientific, 15240). Cells were cultured in spinner flasks (Corning, 3152 or 3153), shake flask (Corning 431143, or 431145) or bioreactors. For spinner/shake flask, cells were cultured at 37° C. incubator with 170 rpm agitation and a humidified atmosphere of 8% CO2; for bioreactors (Eppendorf, DASGIP Parallel Bioreactor system, glass vessels and single use vessels), cell culture was controlled by programed parameters, (DO 40%, pH 7.2, agitation at 130 rpm, 150 rpm or 170 rpm). Typically, cells were seeded at 0.25-0.5×10$^6$/mL, subcultured every 2-3 days by adding fresh cell culture medium when cell density reached approximately 2-3×10$^6$/mL. Cell density and viability were determined using a Vi-cell™ XR cell viability Analyzer (Beckman Coulter).

Plasmids: Three plasmids were used to produce recombinant adeno-associated viral vectors (rAAV): 1) Transgene plasmid containing hFVIII flanked by ITRs, 2) A packaging plasmid containing rep and cap genes, 3) An adenoviral helper plasmid containing adenovirus E2, E4 and VARNA genes. All plasmids were purchased from and manufactured by Aldevron.

Preparation of PEI solutions: Linear polyethylenimine (PEI) "Max" 40 KDa (Polysciences, 24765-2, hydrochloride salt of the linear PEI 25 KDa) was used as transfection reagent. For transfection optimization studies, PEI "Max" was dissolved in 5 mM Tris to make a 0.5 mg/mL solution and the solution was adjusted to different pH, including pH7.0, 7.1, 7.2, 7.3, 7.4, 7.6, 7.8, or 8.0. After several studies, PEI solution at pH 7.1 was selected for all studies if not specified because of the best transfection and rAAV production.

Using enhancing agents in PEI-mediated transfection: The potential transfection enhancing agents evaluated for their effect on transfection and rAAV production were enhancer 1 and 2 in ExpiFectamine™ 293 Transfection Kit (Thermo Fisher Scientific, A14525), P3000 reagent in Lipofectamine® 3000 Transfection Kit (Thermo Fisher Scientific, L3000015), enhancer in Effectene™ Transfection Reagent Kit (Qiagen, 301427). Also studied were a variety of compounds including valproic acid, etoposide, teniposide, siomycin A and vorinostat to test their effectiveness on PEI cell transfection and rAAV production.

HEK 293F cells were grown in F17 medium plus 1× GlutaMAX™ Supplement and 1× Antibiotic-antimycotic in spinner flasks or shake flasks. The day before transfection, cells were seeded at 0.5-2×10$^6$ cells/mL by adding fresh medium. After 24 hr, cells were transfected at a cell density of 1-4×10$^6$ cells/mL. Three plasmids for transfection, hFVIII, Rep/cap, Ad2 helper, were used at a molar ratio of 1:1:1, 0.5:1:1 and 1:2:2, and at weight ratio of 0.75:0.75:0.75, 1:1:1 and 1.5:1.5:1.5. The total DNA amount used for transfection was from 0.5 to 4.2 μg per mL of cell culture volume. PEI/DNA complex was prepared with different weight ratios of PEI and DNA, at 1:1, 1.5:1, 2:1, 2.5:1 and 3:1, incubated at room temperature for 1, 5, 10, 15, 20, 25 and 30 minutes, then the DNA/PEI complexes were added to the cell culture. Free PEI (without DNA) from 0.5 to 5.6 μg/mL was added to the cell culture immediately after DNA/PEI complexes. Enhancing agents were added directly to the cells at the time of transfection or 24 hr before transfection or 16-18 hr after transfection. Different amounts of enhancing agents were studied. Samples, including cells and cell culture media, were taken at 48 and 72 hr post transfection for cell count and cell viability and cell culture was harvested at 72 hr post transfection.

Production of rAAV vectors in bioreactors: A 2 L DAS-GIP Parallel Bioreactor system (Eppendorf) equipped with two or three pitched blade impellers was used to scale up the vector production process. The final working volume was adjusted to 400 mL or 1.2 L. The agitation was set to 130 rpm, 150 rpm or 170 rpm, the temperature was maintained at 37° C. pHI was tested at 6.3, 6.8, 7.2, 7.4, 7.6 or 8. pH7.2 was selected due to the best cell growth and rAAV production. Dissolved oxygen was maintained at 40% by supplementation with a gas mix of oxygen, carbon dioxide and air. All these parameters were monitored and controlled by DASGIP Control System with DASGIP Control 4.0 software. HEK 293F cells cultured in F17 medium were inoculated at a cell density of 0.4×10$^6$ cells/mL with viability greater than 95%. Cells were subcultured at day 3 after seeding by adding fresh medium. Cell density was adjusted to approximately 0.5-1.7×10$^6$ cells/mL after subculture. Twenty-four hours post subculture, cells were transfected with PEI/DNA complex, free PEI and transfection enhancers as described above and in the drawing legends. The cell density was approximately 1-3×10$^6$ cells/mL at transfection. 1.2 to 4.2 μg/mL of DNA, PEI/DNA weight ratio of 1:1, 1.5:1, 2:1, 2.5:1 or 3:1 with 0.5-4.2 μg/ml free PEI and enhancing agents were analyzed for plasmid transfection and rAAV production. Cell culture was harvested at 72 hr post-transfection.

Quantitation of rAAV vectors: rAAV vectors were released from the transfected HEK 293F cell harvest by either microfluidization (microfluidizer™, Microfluidics) or three times sonication. The cell debris was pelleted by centrifugation and the supernatants were collected and analyzed by real-time PCR.

rAAV vector genome copy number was determined with real-time polymerase chain reaction (Q-PCR) (Thermo Fisher Scientific, QuanStudio 7) using TaqMan Master Mix (Thermo Fisher Scientific, 4304437). 10 μL of cell lysate was first treated with 2 μl of universal RNA (Biochain, R423565) and then with 7.6 U DNase I (Qiagen, 79254) to digest contaminating unpackaged DNA. The solution was then treated with 0.2% SDS/5 mM EDTA/0.2M NaCl and heated at 95° C. for 10 min to inactivate DNase I and release vector DNA. The primers and probe detected transgene hFVIII sequence: Forward primer: 5'-TGAGGAGGCT-GAAGACTAT-3' (SEQ ID NO: 3), reverse primer 5'-CCACAGACCTGATCTGAATGAA-3' (SEQ ID NO:4) and probe/5'-6FAM/TGGATGTGG/ZEN/TGAGGTTT-GATGATGACA/3IABKFQ/-3' (SEQ ID NO: 5). The standard was generated by linearizing pAAV-hFVIII plasmid. All samples were performed in triplicate.

Western blot analysis: rAAV vectors were released from the transfected HEK 293F cell harvest by either microfluidization (microfluidizer™, Microfluidics) or three times sonication. The cell debris was pelleted by centrifugation and the supernatants were collected for Western blot. Cell lysate was mixed with 4× NuPAGE LDS Sample buffer (Thermo Fisher Scientific, NP0007) and then heated at 95° C. for 5 min. The samples were separated by SDS-PAGE and transferred to PVDF membrane (Thermo Fisher Scientific, LC2002). After blocking with Odyssey blocking buffer (Li-COR Biosciences, 927-50000) for 1hr, the membranes were incubated at room temperature for 2 hr with a mouse monoclonal anti-AAV VP1,2,3 antibody at a 1:500 dilution (American Research Products, Inc., 03-65158). After three rinses, the membranes were incubated at room temperature for 1hr with goat anti-mouse IgG, Alexa Fluo® 680 conjugate secondary antibody at a 1:5000 dilution (Invitrogen, A21057). The membranes were scanned with Odyssey® CLx imager (Li-COR Biosciences).

Example 2

Transfection Enhancers Increased rAAV-FVIII Vector Productivity.

A highly efficient PEI-based transfection method using PEI "Max" as transfection reagent was developed to transfect three plasmids into HEK 293F cells in F17 medium to produce rAAV vectors. The best cell culture window for plasmid transfection to obtain the highest rAAV productivity has been described. However, when used to generate rAAV-FVIII vectors, vector productivity was relatively low (vector titer at 2-3E+10 vg/mL). The cause of low productivity may be because the FVIII transgene is quite large compared to other transgenes like eGFP, FIX.

A search for agents that can improve transfection efficiency was undertaken. Different transfection enhancers in several transfection kits including ExpiFectamine™ 293 Transfection Kit, Lipofectamine® 3000 Transfection Kit and Effectene™ Transfection Reagent Kit were evaluated. The data show that the transfection enhancers in ExpiFectamine™ 293 Transfection Kit can significantly increase rAAV vector production. Enhancers in other transfection kits did not meaningfully improve rAAV production. ExpiFectamine™ 293 Enhancer 1 and 2 were used at 1:200 and 1:20 of culture volume, respectively. Enhancer 1 and 2 in ExpiFectamine™ 293 Transfection Kit at the time of transfection increased rAAV titer 2-3 fold compared with adding them at 16-18 hr post-transfection or no enhancers (FIG. 1). Adding enhancer 1 and 2 before transfection did not detectably increase rAAV production. Enhancer 1 and Enhancer 2 are components of ExpiFectamine™ 293 Transfection Kit that is a cationic, lipid-based transfection reagent kit for protein expression from Expi293F™ cells cultured in Expi293™ Expression Medium. The enhancers are stated by the manufacturer to be animal origin-free, chemically defined, protein-free, serum-free reagents. These enhancers were used in a new application that is different from the original design for this Kit. These enhancers were used to generate rAAV vectors instead of expressing proteins. The kit suggests to use Enhancer 1 and 2 at 16 to 18 hours post-transfection to boost transfection and protein expression. However, the studies disclosed herein show that enhancer 1 and enhancer 2 added simultaneously at the time of transfection resulted in the highest rAAV production, 2 to 3 fold higher than post-transfection usage, suggesting that the enhancers play a different role in rAAV production from protein expression. Adding these enhancers to a PEI-mediated transfection method set forth herein and in PCT/US16/64414 increased transfection of a large transgene plasmid into cells resulting in a substantial increase in rAAVs.

Transfection parameters including cell density at transfection, DNA amount, PEI/DNA ratio, free PEI amount in the presence or absence of these enhancers were further optimized. The data show that increased cell density at transfection and PEI/DNA ratio, using less DNA and free PEI yielded the greatest rAAV productivity in the presence of the enhancers.

Figure 2:
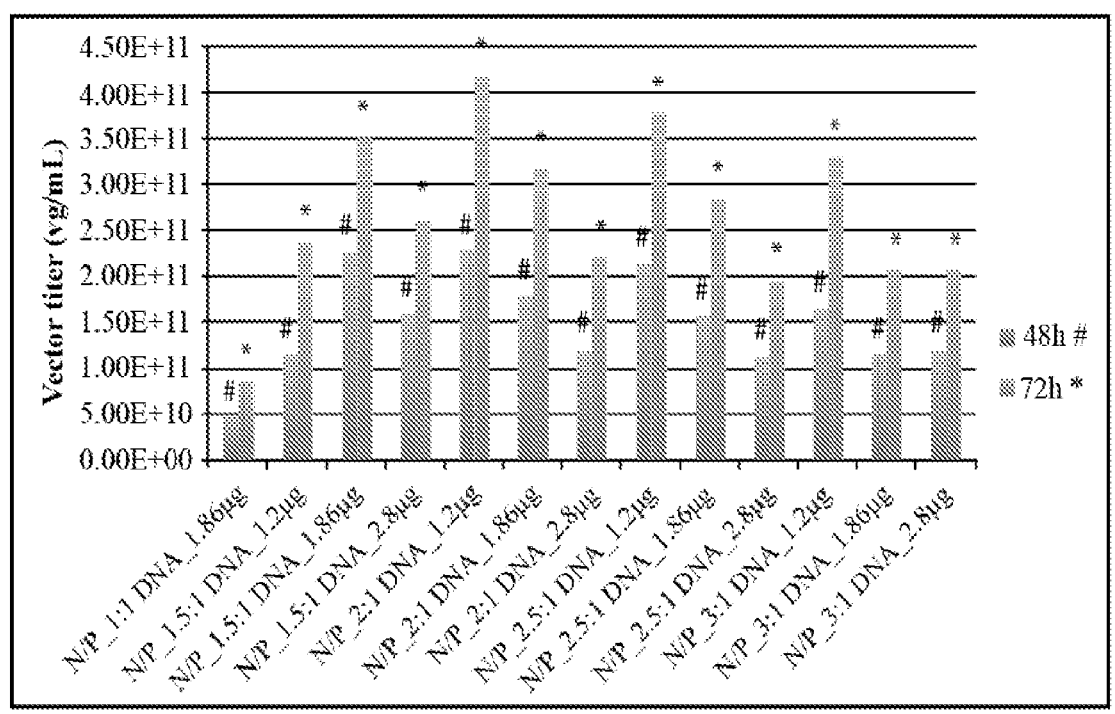
FIG. 2 shows optimization of rAAV-FVIII vector production using different DNA amounts and PEI/DNA ratios. HEK 293F cells in spinner flasks were transfected with a total DNA amount of 1.2, 1.86, or 2.8 µg/mL DNA, respectively, using three plasmids. Plasmid DNA ratio was the same as described previously. However, PEI/DNA ratios used in this study were 1:1, 1.5:1, 2:1, 2.5:1 and 3:1. The free PEI used was 1.5 µg/mL. Enhancer 1 and 2 from Expi-Fectamine™ 293 Transfection Kit were used as described above. The cell density was 2-3×10$^6$ cells/mL at transfection. The samples were taken at 48 h (#) or 72 h (*) post-transfection and rAAV vector titer determined by Q-PCR assay. The highest rAAV vector yields were observed under conditions of 1.2 µg/mL of DNA a PEI/DNA ratio of 2-2.5:1, and with enhancers.

FIG. 2 shows rAAV-FVIII vector production using different DNA amount and PEI/DNA ratio in spinner flask determined by qPCR. HEK 293F cells in spinner flasks were transfected with 1.2, 1.86, 2.8 µg/mL of DNA, PEI/DNA (N/P) ratio used was 1:1, 1.5:1, 2:1, 2.5:1, 3:1 and 1.5 µg/mL of free PEI. Enhancer 1 and 2 in ExpiFectamine™ 293 Transfection Kit were added into cells at transfection. Enhancer 1 and enhancer 2 were used at 1:200 and 1:20 of culture volume, respectively. The cell density was $2.5-3 \times 10^6$ cells/mL at transfection. The best condition for vector production resulted from using 1.2 µg/mL of DNA with PEIDNA ratio 2-2.5:1 and 1.5 µg/mL free PEI and enhancer 1 (1:200 dilution) and 2 (1:20 dilution) at transfection.

Figure 3:
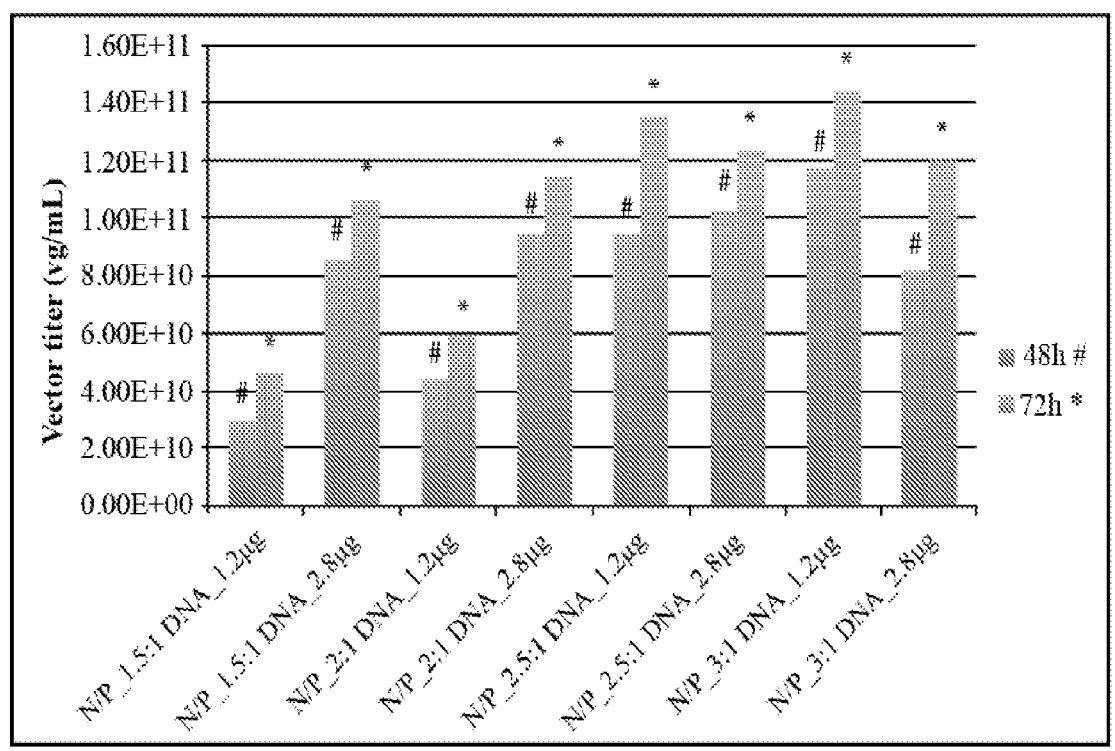
FIG. 3 confirms rAAV-FVIII vector productivity in a bioreactor. HEK 293F cells were cultured in bioreactors at a scale of 400 mL and transfected with three plasmids, (total plasmid DNA amount of 1.2 or 2.8 µg/mL). Plasmid DNA molar ratio of 1:1:1, PEI/DNA (weight) ratio of 1.5:1, 2:1, 2.5:1 and 3:1 were used. Free PEI of 1.5 µg/mL and Enhancers 1 and 2 were also used as described previously. The cell density was 2-3×10$^6$ cells/mL at transfection. The highest vector production (Q-PCR data) was observed under conditions of 1.2 µg/mL of total DNA with PEIDNA ratios of 2.5-3:1.

Conditions in 2 L DASGIP bioreactors were evaluated and further optimized at a larger scale. FIG. 3 shows rAAV-FVIII vector production using different DNA amount and PEI/DNA ratio in bioreactors determined by qPCR. HEK 293F cells were cultured in 400 mL F17 at 37° C., pH 7.2, DO 40%, agitation of 150 rpm in bioreactors. Cells were transfected with DNA molar ratio of 1:1:1 and 1.2 or 2.8 µg/mL of DNA, PEI/DNA (N/P) ratio of 1.5:1, 2:1, 2.5:1 or 3:1 and 1.5 µg/mL of free PEI. Enhancer 1 and 2 in ExpiFectamine™ 293 Transfection Kit were added into cells at transfection. Enhancer 1 and enhancer 2 were used at 1:200 and 1:20 of culture volume, respectively. Cell density was $2-3 \times 10^6$ cells/mL at transfection. The condition which resulted with the highest rAAV vector productivity was using a DNA molar ratio of 1:1:1 and 1.2 µg/mL of DNA with PEI/DNA ratio of 2.5-3:1 and 1.5 µg/mL free PEI and enhancers.

Figure 4:
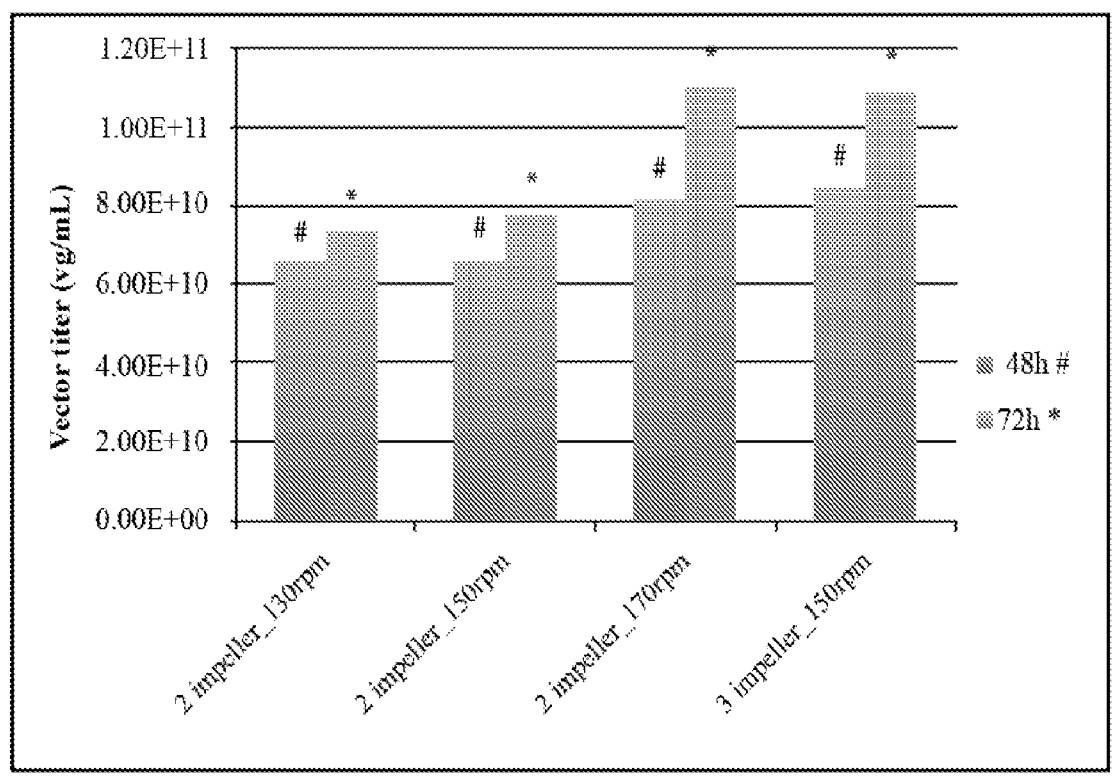
FIG. 4 shows that high rAAV vector productivity remains at full scale of DASGIP bioreactor. The optimized transfection conditions were further evaluated for rAAV production at 1.2 Liter (L) scale, the full scale of DASGIP bioreactor. HEK 293F cells were cultured in DASGIP bioreactors at 1.2 L scale with 2 or 3 impellers at 130 rpm, 150 rpm and 170 rpm agitation speeds. Cells were transfected with three plasmids of 1.2 µg/mL total plasmid DNA, PEI/DNA ratio of 2.5:1 was used to prepare the PEI/DNA complex; DNA molar ratio and amount of free PEI and transfection enhancers were as described previously. The Q-PCR data indicated that the vector productivity at the scale of 1.2 L remained comparable to that observed at smaller scales, indicating that the optimized transfection can be scaled up. Although not wishing to be bound by any theory, Q-PCR data also suggested that high agitation speed may further enhance vector productivity.

Cell culture volume was increased from 400 mL to 1.2 L in bioreactors to produce rAAVs. HEK 293F cells were cultured at 37° C., pH 7.2, DO 40%, agitation of 130 rpm, 150 rpm or 170 rpm with 2 or 3 impellers. Cells were transfected with a DNA molar ratio of 1:1:1, 1.2 µg/mL of DNA, PEI/DNA (N/P) ratio of 2.5:1 and 1.5 µg/mL of free PEI. Enhancer 1 and 2 in ExpiFectamine™ 293 Transfection Kit were used as described above. FIG. 4 shows rAAV titers from these studies. The data demonstrated that the optimized conditions from a small scale of 50 mL in spinner flask can be scaled-up to 400 mL and then up to 1.2 L scale. Using enhancing agents in the optimized PEI-mediated transfection conditions can increase rAAV vector productivity by 8-10 fold in serum-free suspension culture. This process is highly efficient, safe and scalable.

Figure 5:
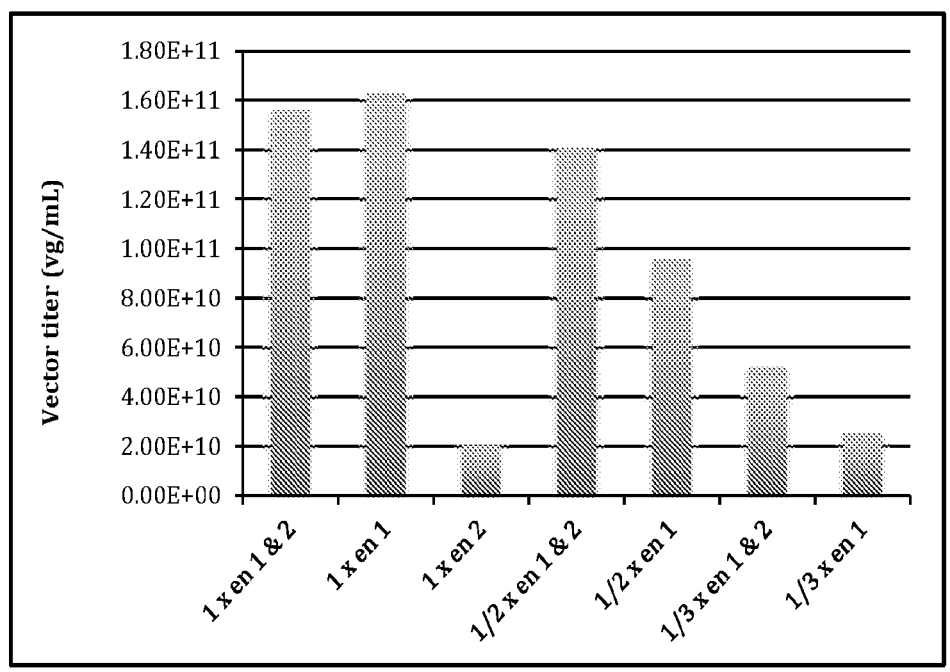
FIG. 5 shows enhancer 1 alone improved rAAV productivity to the same level as that produced when both enhancers 1 and 2 used. To further optimize rAAV production method, studies were performed using only one enhancer: either enhancer 1 or enhancer 2 alone at transfection, to compare the vector productivity with that when both enhancers were used. The Q-PCR data indicated that rAAV productivity when enhancer 1 was used was comparable to that when both enhancer 1 and 2 were used. However, enhancer 2 only resulted in lower rAAV production, suggesting that enhancer 2 does not have a positive impact on rAAV production. In addition, reducing the amount of enhancers 1 and 2 at transfection resulted in lower rAAV titer.
Figure 6:
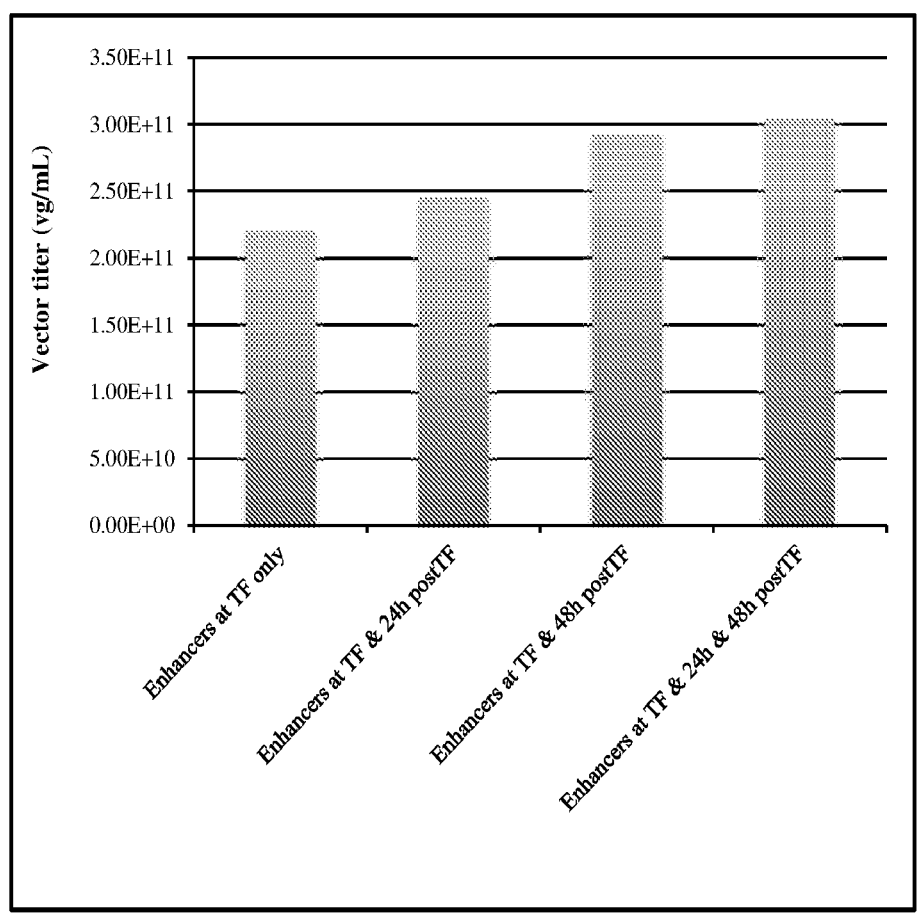
FIG. 6 shows that repetitive use of enhancers 1 and 2 at both transfection (TF) and at 24 hr or at 48 hr post-transfection, or enhancers 1 and 2 used repetitively for three times, at transfection and at 24 hr and 48 hr post-transfection, slightly increased rAAV titers. Enhancer 1 and 2 were used at 1:200 and 1:20 of culture volume, respectively at transfection first. The additional amount of enhancers 1 and 2 were added at 24 hr, or at 48 hr or both at 24 hr and 48 hr post-transfection to the cell culture. The transfection conditions used in this study are described in FIG. 5. The Q-PCR data indicated that rAAV vector productivity increased slightly (less than 1-fold increase) with repetitive use of enhancers.

To determine whether both enhancer 1 and 2 were needed at transfection to improve rAAV production and further define the amount of these enhancers, they were evaluated individually. The data show that enhancer 1 alone can improve rAAV productivity to the same level as both enhancer 1 and 2 combined. Enhancer 2 alone did not detectably increase rAAV production (FIG. 5). The amount of enhancer 1 and 2 were also reduced to further define the optimal condition of the process. Reduced amount of enhancer 1 and 2 resulted in lower rAAV titer (FIG. 5). Increased amount of enhancer 1 (1:100 or 1:150 dilution) and 2 (1:10 or 1:15 dilution) at transfection did not detectably improve the rAAV productivity. In addition to using enhancer 1 and 2 at transfection, they were evaluated at 24 hr, or 48 hr or both 24 hr and 48 hr post-transfection to determine if they can further increase rAAV titer. FIG. 6 shows that repetitive use of enhancers slightly increased rAAV production.

Example 3

Valproic Acid Improves rAAV-FVIII Vector Productivity.

Figure 7:
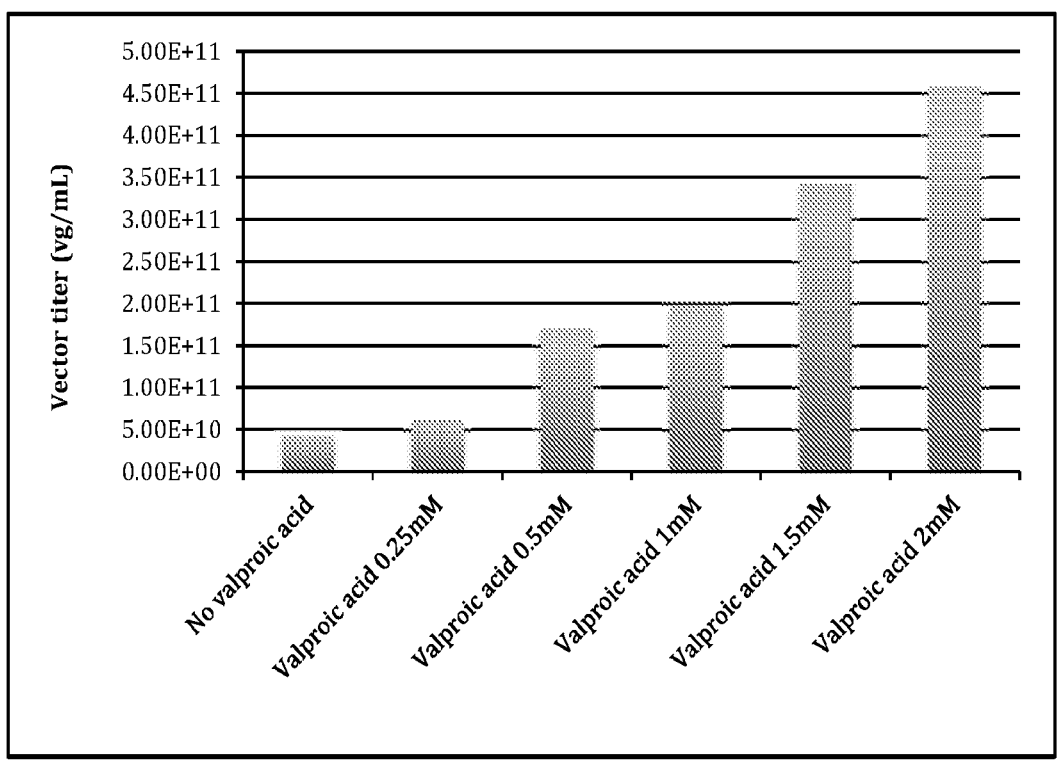
FIG. 7 shows data indicating valproic acid enhanced rAAV production. HEK 293F cells in spinner flask were transfected with three plasmids using PEI transfection method as described previously. No enhancers from Expi- Fectamine™ 293 Transfection Kit were used in this study. Valproic acid at different concentrations was added to cells at transfection. Cells were transfected with 1.2 µg/mL of total three plasmid DNA, DNA molar ratio of three plasmids was 1:1:1, PEI/DNA (weight) ratio was 2:1 and 1.5 µg/mL of free PEI were used. Valproic acid from 0.25 mM to 2 mM was evaluated. The Q-PCR data indicated that, when 2 mM valproic acid was used in transfection, a 10-fold higher rAAV vector production was observed in comparison to the amount of vector produced in the absence of valproic acid.
Figure 8:
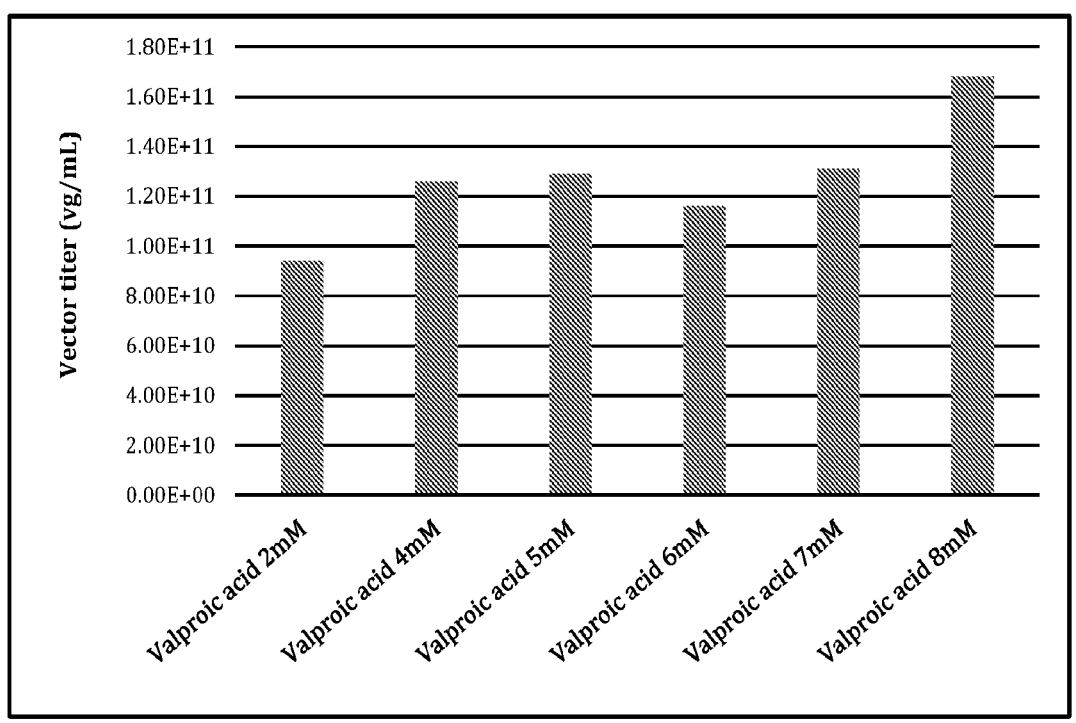
FIG. 8 shows rAAV-FVIII vector production at different concentrations of valproic acid, as determined by qPCR. Valproic acid from 2 mM to 8 mM (2 mM, 3 mM, 4 mM, 5 mM, 6 mM, 7 mM and 8 mM) was used at transfection of HEK 293F cells in a 1 L bioreactor culture. Valproic acid >4 mM resulted in 1.2-1.8 fold higher AAV vector production compared with 2 mM of valproic acid. 1.2 µg/mL of DNA, DNA molar ration of 1:1:1, PEI/DNA weight ratio of 2.5 and 1.5 µg/mL free PEI were used in this study.

A variety of compounds including valproic acid, etoposide, teniposide, siomycin A and vorinostat were evaluated to determine their effect on transfection and rAAV production. Among these compounds, valproic acid significantly increased rAAV productivity. Valproic acid is an inhibitor of histone deacetylase and also a FDA-approved drug to treat seizures. Different concentrations of valproic acid, 0.25 mM, 0.5 mM, 1 mM, 1.5 mM, 2 mM, 5 mM, 7.5 mM and 10 mM were used at transfection in spinner/shake flask culture and also in DASGIP bioreactor culture. Using valproic acid in the optimized PEI-mediated transfection increased rAAV-FVIII vector titer around 10-fold compared to that without any enhancers, and reached the same rAAV productivity level or higher as with enhancer 1 and 2 in serum-free suspension culture system (FIG. 7). 1.2 µg/mL of DNA, DNA molar ratio of 1:1:1, PEI/DNA weight ratio of 2:1 or 2.5:1 and 1.5 µg/mL of free PEI were used in these valproic acid studies. After PEIDNA complex and free PEI were added to the cells at transfection, valproic acid at different concentrations was added. No enhancers from ExpiFectamine™ 293 transfection kit were used in this study. FIG. 8 shows improved AAV vector production at increased valproic acid concentrations in a 1L bioreactor culture, e.g. 4 mM or higher valproic acid, such as 5-8 mM.

Example 4

Enhancer 1 alone of ExpiFectamine™ 293 Transfection Kit and valproic acid used alone in the optimized PEI-based transfection method can increase rAAV vector productivity substantially, about 10-fold higher, than the currently reported production protocol using similar technologies. The use of enhancer 1 or valproic acid alone in the rAAV production system provides a new scalable rAAV production platform which can be used to efficiently produce any serotype of rAAV vectors in serum-free suspension cell culture. This process is especially applicable to producing rAAV vectors with large transgenes and for producing rAAV vectors that are difficult to generate. This process is fully scalable, cGMP compliant and versatile rAAV production system which is feasible for large scale manufacturing of rAAV.

Example 5

The data in FIG. 4 demonstrates that the optimized conditions from a small scale of 50 mL in spinner flask can be scaled-up to 400 mL and then up to 1.2 L scale. Further scalability up to larger volumes can be achieved. For example, it is contemplated that the methods will be scalable up to 2 Liters, 2-20 Liters, 20-50 Liters, or 50-100 Liters. Even larger volumes are contemplated, such as, 100-500 Liters, 500-1,000 Liters, or 1,000 or more Liters. Such scale up may include cloning of cells and selecting clones that produce large quantities of rAAV vector. Creating master cell banks of such clones that express rAAV vector in large quantity provides for a reliable and reproducible source of cells applicable to the invention compositions and methods herein.

Further refinements in cell culture conditions, transfection conditions, cell lysis and/or culture supernatant collection of rAAV vector harvests, removal of impurities and subsequent downstream purification conditions may also contribute to substantial increases in scalability.

Example 6

1.0 Exemplary, Non-Limiting, Process Development Acceptance Criteria, Overview, Flow Description and Parameters Varied for Increasing Production Scale of rAAV Vector (e.g. LK03-FVIII) using Suspension Cells
  1.1 Cell Thaw and Expansion

| Process Criteria | Units | Instrument used for Analysis |
|---|---|---|
| Viable Cell Density (VCD) | Sufficient viable cells/mL to progress to the subsequent expansion step | Vi-CELL ™ XR |

1.2 rAAV Vector Production at a 1.2 L Bioreactor Scale

| Process Criteria | Units | Assay used for Analysis |
|---|---|---|
| Production at Harvest | ≥5 × 10$^{10}$ vg/mL | Viral genome titer by qPCR |

Figure 9:
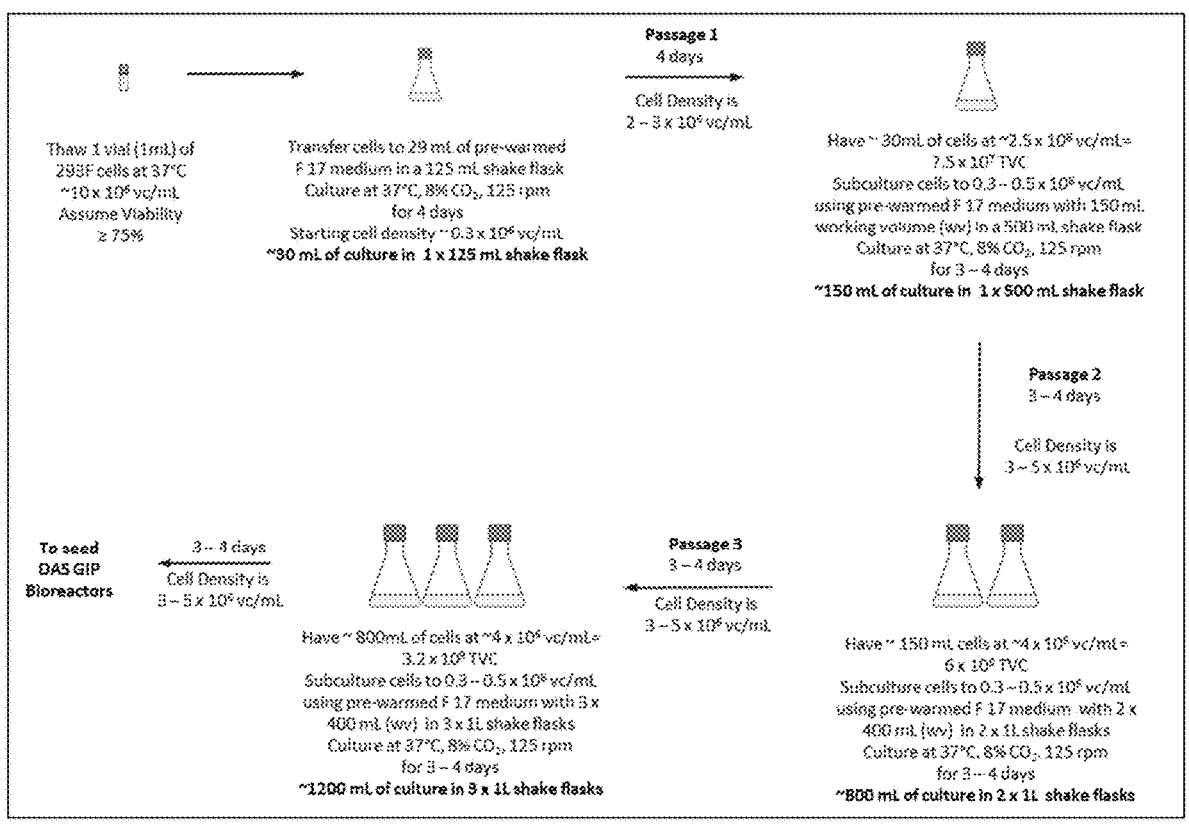
FIG. 9 shows a representative process flow diagram for the Cell Thaw and Cell Expansion portion of an upstream rAAV vector process as disclosed herein.

2.0 Process Overview
  2.1 Cell Thaw and Cell Expansion Process
    2.1.1 Process Flow Diagram
      FIG. 9 is a representative process flow diagram for the Cell Thaw and Cell Expansion portion of an upstream rAAV vector process.

2.1.2 Process Flow Description
      The following is a representative process flow description for the Cell Thaw and Cell Expansion portion of an upstream rAAV vector (e.g. LK03-FVIII) process:

| Step or Operation | Description |
|---|---|
| Cell Thaw | Thaw cells at 37° C. for ≥2.5 min<br>Place cells in 29 mL pre-warmed Freestyle ™ F17 medium with 1X GlutaMAX ™<br>30 mL of cells in a 125 mL shake flask<br>Culture cells at 37° C. for 4 days at 8% CO$_2$ at 125 rpm |
| Passage 1 | Subculture cells to 0.3-0.5 × 10$^6$ vc/mL using pre-warmed Freestyle ™ F17 medium with 1X GlutaMAX ™<br>150 mL of cells in a 500 mL shake flask<br>Culture cells at 37° C. for 3-4 days at 8% CO$_2$ at 125 rpm |
| Passage 2 | Subculture cells to 0.3-0.5 × 10$^6$ vc/mL using pre-warmed Freestyle ™ F17 medium with 1X GlutaMAX ™<br>400 mL of cells in each of 2 × 1000 mL shake flasks (800 mL total)<br>Culture cells at 37° C. for 3-4 days at 8% CO$_2$ at 125 rpm |
| Passage 3 | Subculture cells to 0.3-0.5 × 10$^6$ vc/mL using pre-warmed Freestyle ™ F17 medium with 1X GlutaMAX ™<br>400 mL of cells in each of 3 × 1000 mL shake flasks (1200 mL total)<br>Culture cells at 37° C. for 3-4 days at 8% CO$_2$ at 125 rpm |
| Next Step | Cells from the shaker flasks are used to seed the DAS GIP bioreactors for rAAV vector, e.g., LK03-FVIII, production |

2.1.3 Parameters Varied during Cell Thaw and Cell Expansion Studies
      The following parameters were evaluated during development of the 293-F cell thaw and cell expansion process:

| Step or Operation | Parameter Studied | Ranges Studied (if applicable) |
|---|---|---|
| Cell Thaw | Minimum thawing time | Time needed to see one ice crystal remaining in the vial |
| Cell Thaw | Maximum thawing time | 2X and 3X of minimum time determined |
| Cell Thaw | Time cell bank vials sit on dry ice prior to thawing | 0-2 hours |
| Cell Expansion | Seeding density | 0.1-1.1 × 10$^6$ vc/mL |
| Cell Expansion | Upper cell density limit for seed train culture | 4-6 × 10$^6$ vc/mL |
| Cell Expansion | Shaker Speed range (2.5 cm throw) | 125 ± 15 rpm |

Example 7

Figure 10:
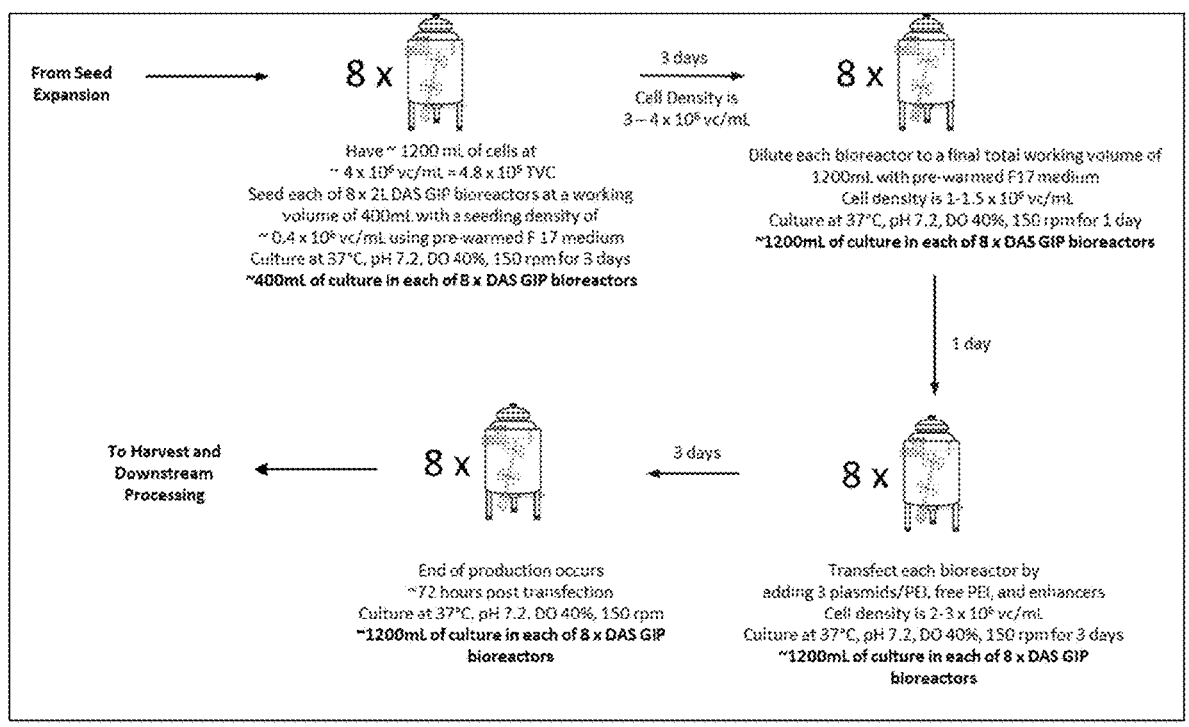
FIG. 10 shows a representative process flow diagram for a 1.2 L bioreactor production of rAAV vector as disclosed herein.

2.3 Exemplary, Non-Limiting, rAAV Vector (e.g. LK03-FVIII) Production at the 1.2L Bioreactor Scale, Process Flow and Parameters Varied for Increased Scale of rAAV Vector Protein
  2.3.1. Process Flow Diagram
    FIG. 10 is a representative process flow diagram for the 1.2 L bioreactor production of rAAV vector (e.g. LK03-FVIII).
  2.3.2 Process Flow Description
    The following is a process flow description for the 1.2 L bioreactor production of rAAV vector (e.g. LK03-FVIII):

| Step or Operation | Description |
|---|---|
| Seed DAS GIP bioreactors (Day 0) | Seed each of 8 × 2L DAS GIP bioreactors with a seeding density of 0.4 × 10⁶ vc/mL using pre-warmed Freestyle™ F17 medium with 1X GlutaMAX™<br>Pluronic™ F-68 added to medium, final 0.1%<br>Working volume is 400 mL<br>Culture cells at 37° C., pH 7.2, DO 40%, 150 rpm for 3 days |
| Dilute and bring bioreactors to full working volume (Day 3) | Dilute each bioreactor to a final working volume of 1200 mL using pre-warmed Freestyle™ F17 medium with 1X GlutaMAX™<br>Cell density is 1-1.5 × 10⁶ vc/mL<br>Culture cells at 37° C., pH 7.2, DO 40%, 150 rpm for 1 day |

-continued

| Step or Operation | Description |
|---|---|
| Transfection (Day 4) | Transfect each bioreactor by adding 3 plasmids/PEI, free PEI, and enhancer(s)<br>Cell density is 2-3 × 10⁶ vc/mL<br>Culture cells at 37° C., pH 7.2, DO 40%, 150 rpm for 3 days |
| End of Production (Day 7) | Each bioreactor is sampled ~72 hours post transfection for production using the viral genome titer via qPCR assay |
| Next Step | The material from each bioreactor proceeds to harvest and downstream processing |

2.3.3 Parameters Varied during rAAV vector (e.g. LK03-FVIII) Production Development Studies The following parameters were evaluated during the development of the 1.2L bioreactor production process for rAAV vector (e.g. LK03-FVIII):

| Step or Operation | Parameter Studied | Ranges Studied (if applicable) |
|---|---|---|
| Culturing cells in the DAS GIP bioreactors | Seeding density | 0.25-0.5 × 10⁶ vc/mL |
| | Agitation rate | 130-170 rpm |
| | pH | 6.3-8.0 |
| | Final working volume | 400 mL, 1200 mL |
| Transfection | PEI solution pH | 7.0-8.0 |
| | Molar ratios of plasmids:FVIII:Rep/cap:Ad2 helper | 1:1:1, 0.5:1:1, 1:2:2 |
| | Weight ratios of plasmids:FVIII:Rep/cap:Ad2 helper | 0.75:0.75:0.75, 1:1:1, 1.5:1.5:1.5 |
| | Weight ratio of PEI/DNA complex | 1:1, 1.5:1, 2:1, 2.5:1, 3:1 |
| | Incubation time of PEI/DNA complex | 1-30 minutes |
| | Total amount of DNA | 0.5-4.2 µg/mL |
| | Amount of free PEI | 0.5-5.6 µg/mL |

| | Enhancers | | Range | Timing of addition |
|---|---|---|---|---|
| | Type Used together | ExpiFectamine™ 293 Kit Enhancer 1 | 1:100-1:800 | 24 hours prior to transfection - 18 hours post transfection |
| | | ExpiFectamine™ 293 Kit Enhancer 2 | 1:10-1:80 | 24 hours prior to transfection - 18 hours post transfection |
| | ExpiFectamine™ 293 Kit Enhancer 1 | | 1:200-1:800 | 24 hours prior to transfection - 18 hours post transfection |
| | Valproic Acid | | 0.25-10 mM | 24 hours prior to transfection - 18 hours post transfection |
| End of Production | Harvest time | | | 48, 72 hours post transfection |

Example 8

Representative AAV capsid (VP1) proteins.

```
AAV-SPK VP1 Capsid
                                                    (SEQ ID NO: 1)
  1 MAADGYLPDWLEDNLSEGIREWWDLKPGAPKPKANQQKQDNGRGLVLPGYKYLGPFNGLD

61 KGEPVNAADAAALEHDKAYDQQLQAGDNPYLRYNHADAEFQERLQEDTSFGGNLGRAVFQ

121 AKKRVLEPLGLVESPVKTAPGKKRPVEPSPQRSPDSSTGIGKKGQQPAKKRLNFGQTGDS

181 ESVPDPQPIGEPPAAPSGVGPNTMAAGGGAPMADNNEGADGVGSSSGNWHCDSTWLGDRV

241 ITTSTRTWALPTYNNHLYKQISNGTSGGSTNDNTYFGYSTPWGYFDFNRFHCHFSPRDWQ

301 RLINNNWGFRPKRLNFKLFNIQVKEVTQNEGTKTIANNLTSTIQVFTDSEYQLPYVLGSA

361 HQGCLPPFPADVFMIPQYGYLTLNNGSQAVGRSSFYCLEYFPSQMLRTGNNFEFSYNFED

421 VPFHSSYAHSQSLDRLMNPLIDQYLYYLSRTQSTGGTAGTQQLLFSQAGPNNMSAQAKNW
```

```
481  LPGPCYRQQRVSTTLSQNNNSNFAWTGATKYHLNGRDSLVNPGVAMATHKDDEERFFPSS

541  GVLMFGKQGAGKDNVDYSSVMLTSEEEIKTTNPVATEQYGVVADNLQQQNAAPIVGAVNS

601  QGALPGMVWQNRDVYLQGPIWAKIPHTDGNFHPSPLMGGFGLKHPPPQILIKNTPVPADP

661  PTTFNQAKLASFITQYSTGQVSVEIEWELQKENSKRWNPEIQYTSNYYKSTNVDFAVNTE

721  GTYSEPRPIGTRYLTRNL
```

AAV-LK03 VP1 Capsid (SEQ ID NO: 2)

```
MAADGYLPDWLEDNLSEGIREWWALQPGAPKPKANQQHQDNARGLVLPGYKYLGPGNGLDKGEP
VNAADAAALEHDKAYDQQLKAGDNPYLKYNHADAEFQERLKEDTSFGGNLGRAVFQAKKRLLEP
LGLVEEAAKTAPGKKRPVDQSPQEPDSSSGVGKSGKQPARKRLNFGQTGDSESVPDPQPLGEPP
AAPTSLGSNTMASGGGAPMADNNEGADGVGNSSGNWHCDSQWLGDRVITTSTRTWALPTYNNHL
YKQISSQSGASNDNHYFGYSTPWGYFDFNRFHCHFSPRDWQRLINNNWGFRPKKLSFKLFNIQV
KEVTQNDGTTTIANNLTSTVQVFTDSEYQLPYVLGSAHQGCLPPFPADVFMVPQYGYLTLNNGS
QAVGRSSFYCLEYFPSQMLRTGNNFQFSYTFEDVPFHSSYAHSQSLDRLMNPLIDQYLYYLNRT
QGTTSGTTNQSRLLFSQAGPQSMSLQARNWLPGPCYRQQRLSKTANDNNNSNFPWTAASKYHLN
GRDSLVNPGPAMASHKDDEEKFFPMHGNLIFGKEGTTASNAELDNVMITDEEEIRTTNPVATEQ
YGTVANNLQSSNTAPTTRTVNDQGALPGMVWQDRDVYLQGPIWAKIPHTDGHFHPSPLMGGFGL
KHPPPQIMIKNTPVPANPPTTFSPAKFASFITQYSTGQVSVEIEWELQKENSKRWNPEIQYTSN
YNKSVNVDFTVDTNGVYSEPRPIGTRYLTRPL
```

What is claimed is:

1. A method for making transfected cells that produce recombinant adeno-associated viral (rAAV) vector, comprising the steps:
   (a) providing a polyethylenimine (PEI)/plasmid mixture of components (i), (ii) and (iii):
      (i) one or more plasmids comprising nucleic acids encoding AAV packaging proteins, adenovirus E2 proteins, adenovirus E4 proteins and/or nucleic acids encoding virus-associated RNA (VA RNA);
      (ii) a plasmid comprising a transgene that encodes a protein or is transcribed into a transcript of interest; and
      (iii) a PEI solution,
   (b) contacting cells with the plasmid/PEI mixture of step (a) to produce a plasmid/PEI cell culture;
   (c) adding valproic acid, a salt or a derivative thereof to the plasmid/PEI cell culture to produce a second mixture, wherein the valproic acid, salt or derivative thereof is added immediately after step (b); and
   (d) incubating said second mixture of step (c);
   thereby making transfected cells that produce rAAV vector.

2. The method of claim 1, further comprising step (e) harvesting said transfected cells produced in step (d) and/or culture medium from the transfected cells produced in step (d) to produce a cell and/or culture medium harvest.

3. The method of claim 1, further comprising step (e) culturing, expanding, isolating or selecting for cells that have been transfected with the plasmids.

4. The method of claim 1, further comprising step (e) isolating and/or purifying recombinant AAV vector from the transfected cells produced in step (d) and/or culture medium and/or from the transfected cells produced in step (d).

5. The method of claim 3, further comprising step (f) isolating and/or purifying recombinant AAV vector from the transfected cells and/or culture medium harvest produced in step (e).

6. The method of claim 1, wherein the transgene encodes a wild-type, or functional variant blood clotting factor, apoE2, TPP1, arginosuccinate synthase, copper transporting ATPase 2, acid alpha-glucosidase, β-Glucocerebrosidase, α-galactosidase or C1 inhibitor serine protease inhibitor.

7. The method of claim 6, wherein the wild-type, or functional variant blood clotting factor is Factor VII, Factor VIII, or Factor IX.

8. The method of claim 1, wherein the valproic acid, salt or derivative thereof is also added to the cells of step (b) prior to the contacting step.

9. The method of claim 1, wherein the valproic acid, salt or derivative thereof is also added after step (a) or added two or more times after step (b).

10. The method of claim 1, wherein said plasmids (i) and (ii) are in a molar ratio range of about 1:0.01 to about 1:100, and wherein the mixture of components (i), (ii) and (iii) has optionally been incubated for a period of time from about 10 seconds to about 4 hours prior to step (b).

11. The method of claim 1, wherein said plasmids of a (i) and a (ii) are in a PEI: plasmid weight ratio in the range of about 0.1:1 to about 5:1, or in a PEI: plasmid weight ratio in the range of about 5:1 to about 0.1:1.

12. The method of claim 1, wherein said plasmids of a (i) and a (ii) are in a PEI: plasmid weight ratio in the range of about 1:1 to about 5:1, or in a PEI: plasmid weight ratio in the range of about 5:1 to about 1:1.

13. The method of claim 1, further comprising adding free PEI to the cells prior to, at the time of or after step (b), or at the time of or after step (c).

14. The method of claim 13, wherein said free PEI is added so that the PEI: plasmid weight ratio is in the range of about 0.1:1 to about 5:1, or is in the range of about 5:1 to about 0.1:1.

15. The method of claim 1, wherein the molar ratio of nitrogen (N) in the Total PEI to phosphate (P) in plasmid: PEI is in the range of about 1:1 to about 50:1 (N: P).

16. The method of claim 13, wherein the amount of free PEI is about 10% to about 90% of the Total PEI.

17. The method of claim 1, wherein said plasmids of a (i) and a (ii) and PEI have been incubated from about 10 seconds to about 4 hours with each other prior to step (a).

18. The method of claim 1, wherein the incubating of step (d) is for at least about 4 hours.

19. The method of claim 1, wherein the cells comprise mammalian cells.

20. The method of claim 1, wherein the cells are human embryonic kidney (HEK) or Chinese hamster ovary (CHO) cells.

21. The method of claim 1, wherein the cells comprise Human Embryonic Kidney (HEK) 293 cells.

22. The method of claim 1, wherein said cells are HEK 293E, HEK 293F or HEK 293T cells.

23. The method of claim 1, wherein the cells are stably or transiently transfected.

24. The method of claim 1, wherein the cells are in suspension culture.

25. The method of claim 1, wherein the cells are adherent.

26. The method of claim 1, wherein said cells are grown or maintained in a serum-free culture medium.

27. The method of claim 1, wherein said cells are at a density in the range of about $1 \times 10^5$ cells/mL to about $1 \times 10^8$ cells/mL when contacted with said plasmid/PEI mixture.

28. The method of claim 1, wherein said one or more plasmids of a (i) comprises a first plasmid comprising the nucleic acids encoding AAV packaging proteins and a second plasmid comprising the nucleic acids encoding helper functions.

29. The method of claim 1, wherein the encoded AAV packaging proteins comprise AAV rep and/or AAV cap.

30. The method of claim 1, wherein the AAV vector further comprises an intron, an expression control element, one or more adeno-associated virus (AAV) inverted terminal repeats (ITRs) and/or a filler polynucleotide sequence.

31. The method of claim 1, wherein the cells are subcultured to a reduced cell density prior to contact with said plasmid/PEI mixture.

32. The method of claim 1, wherein the cells are contacted with said plasmid/PEI mixture between a period of 2 days to 5 days after subculture.

33. The method of claim 13, wherein the amount of recombinant AAV vector produced is at least 50% or greater with the step of adding free PEI to the plasmid/PEI cell culture compared to without adding free PEI to the plasmid/PEI cell culture.

34. The method of claim 1, wherein the amount of recombinant AAV vector produced is 1-5, 5-8, 8-10 or 10-15 fold greater with the step of adding the valproic acid, salt or derivative thereof compared to without adding the valproic acid, salt or derivative thereof to the plasmid/PEI cell culture.

35. The method of claim 1, wherein the valproic acid is a derivative thereof.

36. The method of claim 1, wherein the valproic acid salt comprises a sodium or potassium salt.

37. The method of claim 35, wherein the valproic acid derivative comprises an amino acid linked or conjugated thereto.

* * * * *

SEQUENCE LISTING

```
<160> NUMBER OF SEQ ID NOS: 5

<210> SEQ ID NO 1
<211> LENGTH: 738
<212> TYPE: PRT
<213> ORGANISM: Adeno-Associated Virus

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65              70                  75                  80

Gln Gln Leu Gln Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Ser Pro Val Lys Thr Ala Pro Gly Lys Lys Arg
    130                 135                 140

Pro Val Glu Pro Ser Pro Gln Arg Ser Pro Asp Ser Ser Thr Gly Ile
145             150                 155                 160
```

-continued

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Ala Pro Ser Gly Val Gly Pro Asn Thr Met Ala Ala Gly Gly
            195                 200                 205

Gly Ala Pro Met Ala Asp Asn Asn Glu Gly Ala Asp Gly Val Gly Ser
        210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Asn Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

```
Glu Gln Tyr Gly Val Val Ala Asp Asn Leu Gln Gln Gln Asn Ala Ala
                580                 585                 590

Pro Ile Val Gly Ala Val Asn Ser Gln Gly Ala Leu Pro Gly Met Val
            595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 2
<211> LENGTH: 736
<212> TYPE: PRT
<213> ORGANISM: Adeno-Associated Virus

<400> SEQUENCE: 2

Met Ala Ala Asp Gly Tyr Leu Pro Asp Trp Leu Glu Asp Asn Leu Ser
1               5                   10                  15

Glu Gly Ile Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205
```

```
Ala Pro Met Ala Asp Asn Asn Glu Gly Ala Asp Gly Val Gly Asn Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
            275                 280                 285
Cys His Phe Ser Pro Arg Asp Trp Gln Arg Leu Ile Asn Asn Asn Trp
290                 295                 300
Gly Phe Arg Pro Lys Lys Leu Ser Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
                340                 345                 350
Val Leu Gly Ser Ala His Gln Gly Cys Leu Pro Pro Phe Pro Ala Asp
            355                 360                 365
Val Phe Met Val Pro Gln Tyr Gly Tyr Leu Thr Leu Asn Asn Gly Ser
        370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Gln Phe Ser Tyr Thr Phe Glu
                405                 410                 415
Asp Val Pro Phe His Ser Ser Tyr Ala His Ser Gln Ser Leu Asp Arg
                420                 425                 430
Leu Met Asn Pro Leu Ile Asp Gln Tyr Leu Tyr Tyr Leu Asn Arg Thr
            435                 440                 445
Gln Gly Thr Thr Ser Gly Thr Thr Asn Gln Ser Arg Leu Leu Phe Ser
    450                 455                 460
Gln Ala Gly Pro Gln Ser Met Ser Leu Gln Ala Arg Asn Trp Leu Pro
465                 470                 475                 480
Gly Pro Cys Tyr Arg Gln Gln Arg Leu Ser Lys Thr Ala Asn Asp Asn
                485                 490                 495
Asn Asn Ser Asn Phe Pro Trp Thr Ala Ala Ser Lys Tyr His Leu Asn
            500                 505                 510
Gly Arg Asp Ser Leu Val Asn Pro Gly Pro Ala Met Ala Ser His Lys
        515                 520                 525
Asp Asp Glu Glu Lys Phe Phe Pro Met His Gly Asn Leu Ile Phe Gly
    530                 535                 540
Lys Glu Gly Thr Thr Ala Ser Asn Ala Glu Leu Asp Asn Val Met Ile
545                 550                 555                 560
Thr Asp Glu Glu Glu Ile Arg Thr Thr Asn Pro Val Ala Thr Glu Gln
                565                 570                 575
Tyr Gly Thr Val Ala Asn Asn Leu Gln Ser Ser Asn Thr Ala Pro Thr
            580                 585                 590
Thr Arg Thr Val Asn Asp Gln Gly Ala Leu Pro Gly Met Val Trp Gln
        595                 600                 605
Asp Arg Asp Val Tyr Leu Gln Gly Pro Ile Trp Ala Lys Ile Pro His
610                 615                 620
Thr Asp Gly His Phe His Pro Ser Pro Leu Met Gly Gly Phe Gly Leu
```

```
                625                 630                 635                 640
Lys His Pro Pro Pro Gln Ile Met Ile Lys Asn Thr Pro Val Pro Ala
                    645                 650                 655

Asn Pro Pro Thr Thr Phe Ser Pro Ala Lys Phe Ala Ser Phe Ile Thr
                660                 665                 670

Gln Tyr Ser Thr Gly Gln Val Ser Val Glu Ile Glu Trp Glu Leu Gln
                    675                 680                 685

Lys Glu Asn Ser Lys Arg Trp Asn Pro Glu Ile Gln Tyr Thr Ser Asn
                690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Pro Leu
                        725                 730                 735

<210> SEQ ID NO 3
<211> LENGTH: 19
<212> TYPE: DNA
<213> ORGANISM: Artificial Sequence
<220> FEATURE:
<223> OTHER INFORMATION: Transgene hFVIII forward primer

<400> SEQUENCE: 3
tgaggaggct gaagactat                                                      19

<210> SEQ ID NO 4
<211> LENGTH: 22
<212> TYPE: DNA
<213> ORGANISM: Artificial Sequence
<220> FEATURE:
<223> OTHER INFORMATION: Transgene hFVIII reverse primer

<400> SEQUENCE: 4
ccacagacct gatctgaatg aa                                                  22

<210> SEQ ID NO 5
<211> LENGTH: 27
<212> TYPE: DNA
<213> ORGANISM: Artificial Sequence
<220> FEATURE:
<223> OTHER INFORMATION: Transgene hFVIII probe

<400> SEQUENCE: 5
tggatgtggt gaggtttgat gatgaca                                             27
```